(12) United States Patent
Bublitz et al.

(10) Patent No.: US 10,244,940 B2
(45) Date of Patent: Apr. 2, 2019

(54) OPTICAL COHERENCE TOMOGRAPHY FOR MEASUREMENT ON THE RETINA

(71) Applicant: CARL ZEISS MEDITEC AG, Jena (DE)

(72) Inventors: Daniel Bublitz, Rausdorf (DE); Christoph Nieten, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 15/546,365

(22) PCT Filed: Jan. 28, 2016

(86) PCT No.: PCT/EP2016/051834
§ 371 (c)(1),
(2) Date: Jul. 26, 2017

(87) PCT Pub. No.: WO2016/120401
PCT Pub. Date: Aug. 4, 2016

(65) Prior Publication Data
US 2018/0020912 A1  Jan. 25, 2018

(30) Foreign Application Priority Data

Jan. 28, 2015 (DE) .......... 10 2015 101 251

(51) Int. Cl.
*A61B 3/10* (2006.01)
*G01B 9/02* (2006.01)

(52) U.S. Cl.
CPC .......... *A61B 3/102* (2013.01); *G01B 9/02004* (2013.01); *G01B 9/0205* (2013.01);
(Continued)

(58) Field of Classification Search
CPC .......... A61B 3/14; A61B 3/0025; A61B 3/12; A61B 3/102; A61B 3/0058
(Continued)

(56) References Cited

U.S. PATENT DOCUMENTS 9,155,465 B2 * 10/2015 Abramoff .............. A61B 3/102
2008/0285043 A1   11/2008 Fercher et al.
(Continued)

FOREIGN PATENT DOCUMENTS

DE   102005058220 A1   6/2007
DE   102010055350 A1   6/2012
(Continued)

OTHER PUBLICATIONS

PCT International Preliminary Report on Patentability for International Application No. PCT/EP2016/051834, dated Aug. 10, 2017, 13 pages.
(Continued)

*Primary Examiner* — Mohammed A Hasan
(74) *Attorney, Agent, or Firm* — Patterson Thuente Pedersen, P.A.

(57) ABSTRACT

An optical coherence tomograph that provides wavelength tunable source radiation and an illumination and measurement beam path, a dividing element that divides source radiation into illumination radiation and reference radiation, and collects measurement radiation. The illumination and measurement beam path has scanner. A detection beam path receives measurement radiation and reference radiation and conducts them onto at least one flat panel detector in a superposed manner. A beam splitter separates the measurement radiation from the illumination radiation. The beam splitter conducts the separated measurement radiation to the detection beam path and sets the numerical aperture of the illumination of the illumination field in the eye. An optical element sets the numerical aperture with which the measurement radiation is collected in the eye and a multi-perforated aperture defines the size of an object field and a number of object spots, from which the measurement radiation reaches the flat panel detector.

37 Claims, 13 Drawing Sheets

(52) U.S. Cl.
CPC ..... *G01B 9/02034* (2013.01); *G01B 9/02041* (2013.01); *G01B 9/02091* (2013.01); *G01B 2290/45* (2013.01)

(58) Field of Classification Search
USPC .......................................................... 351/206
See application file for complete search history.

(56) References Cited

U.S. PATENT DOCUMENTS

| | | | |
|---|---|---|---|
| 2013/0003077 A1 | 1/2013 | Suehira et al. | |
| 2013/0335706 A1 | 12/2013 | Schmitt-Manderbach et al. | |
| 2014/0028974 A1 | 1/2014 | Tumlinson | |
| 2014/0104569 A1* | 4/2014 | Yamazaki | A61B 3/14 351/206 |
| 2014/0320816 A1 | 10/2014 | Abramoff et al. | |
| 2016/0135679 A1 | 5/2016 | Frisken et al. | |

FOREIGN PATENT DOCUMENTS

| | | |
|---|---|---|
| WO | WO 2014/179465 A1 | 11/2014 |
| WO | WO 2014/201503 A1 | 12/2014 |

OTHER PUBLICATIONS

English translation of PCT International Preliminary Report on Patentability for International Application No. PCT/EP2016/051834, dated Aug. 10, 2017, 11 pages.

International Search Report for International Application No. PCT/EP2016/051834, dated May 10, 2016; 10 pages.

English translation of International Search Report for International Application No. PCT/EP2016/051834, dated May 10, 2016; 2 pages.

* cited by examiner

OPTICAL COHERENCE TOMOGRAPHY FOR MEASUREMENT ON THE RETINA

RELATED APPLICATIONS

The present application is a National Phase entry of PCT Application No. PCT/EP2015/051834, filed Jan. 28, 2016, which claims priority from DE Patent Application No. 10 2015 101 251.0, filed Jan. 28, 2015, both of said applications being hereby incorporated by reference herein in their entirety.

FIELD OF INVENTION

The invention relates to an optical coherence tomograph for examining a sample, in particular an eye.

Further, the invention relates to a method for optical coherence tomography for examining a sample, in particular an eye.

BACKGROUND

In optical coherence tomography OCT systems the lateral resolution (x and y) is defined by the numeral aperture (NA) of the optical system used. The axial resolution (z), however, is calculated from an interference pattern and as a rule is much greater than the depth of field of the imaging, which in turn depends on the numerical aperture, more precisely is proportional to $1/NA^2$. In the usually used Fourier domain OCT, which uses a broadband or wavelength-adjustable radiation source, the depth resolution is inversely proportional to the spectral bandwidth, more precisely proportional to $\lambda^2/\Delta\lambda$, wherein $\lambda$ is the average wavelength and $\Delta\lambda$ is the bandwidth. Optical coherence tomography (OCT) is an established method for imaging the eye in ophthalmology. It makes a three-dimensional imaging possible, which is very useful for the diagnosis of eye diseases and the progression thereof. To be named in particular here are diseases of the retina, such as glaucoma or age-related macular degeneration.

To measure the retina of the human eye both a high lateral resolution and a high axial resolution are needed. At the same time the detectable and thus illuminated volume is to be as large as possible in terms of depth (along the optical axis); this requires a small numerical aperture (NA) of the optical system. The lateral resolution requires a large numerical aperture. Thus, ultimately, in the state of the art, the extent of the area accessible in terms of depth and the lateral resolution are linked to each other via the numerical aperture of the optical system and cannot be set independently of each other.

An OCT based imaging method is known from US 2014/0028974 A1. A line is projected through an imaging system onto a sample. The backscattered radiation is combined in an interfering manner with reference radiation and guided to a detector, wherein a confocal filtering is carried out in one direction. An astigmatic optical system is used for this. The depth resolution is obtained by optical coherence tomography. In the case of a spectroscopic analysis of the radiation, a two-dimensional detector is used one dimension of which is used for the confocal filtering with respect to the illuminated line area and the other dimension of which resolves the spectral information. Lateral resolution and accessible depth area are also linked in the approach according to US 2014/0028974 A1.

WO 2014/0179465 A1 describes an OCT which operates in the spectral domain, thus analyses the interference of radiations with a spectrometer. The light source emits a bundle of light which consists of a plurality of parallel individual bundles which are imaged onto the sample through the objective lens. A reference arm also guides several parallel individual bundles, with the result that in the end each individual bundle is guided through the device according to the OCT measurement principle and also analysed on the spectrometer. This device is very complicated to align.

In a scanning OCT system the accessible diameter of the pupil of the eye is usually between 1 mm and 1.5 mm. This results in a lateral resolution of approximately 15 µm and an area detectable in terms of depth with an extent of 3 mm. A better lateral resolution would be achieved with a higher numerical aperture of the optical system. However, at the same time, the depth-detectable area would thus be reduced. In addition, aberrations increase with the numerical aperture. In known OCT systems which use a diameter of up to 1.5 mm in the pupil of the eye astigmatism and coma increase for larger pupils even if the defocusing is disregarded as a higher-order aberration. A diffraction-limited resolution can therefore not be achieved.

For particular applications, in particular for the diagnosis of age-related macular degeneration, a high lateral resolution is desired. In order to diagnose an early stage of this disease, a lateral resolution of approximately 5 µm is needed. At the same time, a depth measurement area that can be sampled of approximately 3 mm is required, as it is assumed that age-related macular degeneration is accompanied by blood vessel growth in deeper layers of tissue. In order to detect such vessels, a good signal-to-noise ratio is additionally needed.

SUMMARY OF THE INVENTION

The object of the invention is to specify an optical coherence tomograph for measurement on the retina of the human eye, in which the lateral resolution is improved without limiting the accessible depth area at the same time.

The invention combines several features in order to obtain, by application of optical coherence tomography, a three-dimensional image which has a particularly good resolution laterally, i.e. transverse to the optical axis, and at the same time can cover a very large depth area axially, i.e. along the optical axis, without the need to adjust focusing elements or lenses during the measurement process.

The invention provides for a multi-spot holoscopy OCT. One aspect of the invention comprises the sample being illuminated and imaged at a plurality of object spots simultaneously, wherein the imaging is done in parallel by filtering the radiation by use of a multi-hole diaphragm during the detection. Each object spot is imaged onto a dedicated detector pixel area. In embodiments an oversampling is done, i.e. the resolution of the detector pixel area of each object spot is greater than the diffraction limit of the optical imaging actually allows. In example embodiments an image correction is then obtained from the resolved intensity distribution.

One embodiment of the coherence tomograph comprises: an illumination device for providing source radiation the wavelength of which is tunable, an illumination and measurement beam path which has a dividing element for dividing the source radiation into illumination radiation and reference radiation, illuminates an illumination field in the eye with the illumination radiation and collects illumination radiation backscattered in the eye as measurement radiation, wherein the illumination and measurement beam path comprise a scanner for adjusting the lateral position of the illumination field in the eye and a front optical system, a reference beam path which provides an optical path length, which corresponds to an optical path length from the splitting element to the illumination field and back, for the reference radiation, a detection beam path which receives the measurement radiation from the illumination and measurement beam path and the reference radiation from the reference beam path and guides them, superimposed, onto an area detector.

In one embodiment, the optical coherence tomograph comprises: an illumination device for providing source radiation wherein the illumination device is tunable regarding the wavelength of the source radiation, an illumination and measurement beam path which comprises a dividing element for dividing the source radiation into illumination radiation and reference radiation, projects the illumination radiation to an illuminated field in the eye and collects illumination radiation backscattered in the eye as measurement radiation from an object field, wherein the illumination and measurement beam path comprises a scanner for adjusting the lateral position of the illumination field and the object field in the eye and a front optics. A reference beam path which provides an optical path length for the reference radiation which path length corresponds to an optical distance from the splitting element to the illumination field and back, a detection beam path receiving the measurement radiation from the illumination and measurement beam path and the reference radiation from the reference beam path and superimposes them at a point of superimposition and guides them to a 2D detector.

In embodiments the illumination and measurement beam path further comprises a beam splitter for splitting off the measurement radiation collected from the eye from the illumination radiation projected to the eye, wherein the beam splitter guides the split off measurement radiation to a detection beam path, and a light-distributing element which distributes the illumination radiation into spots, in order to illuminate the illuminated field with a multi-spot pattern.

Some embodiments have the detection beam path further comprising: an intermediate image plane, an optical element which only acts on the measurement radiation and which cooperates with the front optics and sets the numerical aperture with which measurement radiation is collected from the eye, and a diaphragm which is upstream of the 2D detector and is arranged in or close to the intermediate image plane and defines the size of the object area, wherein the diaphragm upstream of the detector is formed as a first multi-hole diaphragm and a first multi-lens array, which bundles the radiation emerging from each hole of the first multi-hole diaphragm onto a dedicated pixel area of the detector for each spot which pixel areas each have a spatial resolution of, for example, 4 to 100 pixels in one direction, in another example, an 2D area of 5 to 50 pixels or of 5 to 40 pixels per direction, is arranged between this multi-hole diaphragm and the 2D detector.

The method comprises providing source radiation, sweeping the wavelength thereof and dividing the source radiation into illumination radiation and reference radiation, projecting the illumination radiation to an illuminated field in the eye and collecting illumination radiation backscattered in the eye as measurement radiation from an object field in the eye, wherein a scanner for adjusting the lateral position of the illuminated field and of the object area in the eye and front optics are used, delaying reference radiation in a reference beam path, and superimposing the measurement radiation with the reference radiation and detecting an interference signal of the superimposed radiations with an 2D detector.

Some embodiments comprise splitting the measurement radiation collected from the eye from the illumination radiation projected to the eye, projecting illumination and collecting the measurement radiation at independent numerical apertures by using an optical element which only acts on the illumination radiation and which cooperates with the front optics and by using an optical element which only acts on the measurement radiation and which cooperates with the front optics.

The radiation of the imaged object spot is superimposed with reference radiation according to the OCT principle, with the result that the detector spots receive an interference signal between measurement radiation and reference radiation.

A 2D detector is used which samples the object spots on the retina. The multi-hole diaphragm of the optical imaging defines these object spots, and the 2D detector is matched, as a whole, to the size of the area covered by the diaphragm with holes and, with respect to its spatial resolution or pixels, to the size of the holes.

A sweepable light sources used, and detector without any dispersive element takes the place of a spectrometer. The detector resolves each single spot by several pixels in the spatial domain x, y or the frequency domain kx, ky. In contrast to WO 2014/149465 A1, the frequency domain is filled in kz in that several frames are taken during one sweep period of the light source. By detecting each spot in x, y or kx, ky, a higher numerical aperture (NA) can be utilized because wavefront corrections can be done numerically and even after the frames had been taken, resulting in higher resolution and larger depth area.

In embodiments, the illumination beam path and the detection beam path are the same and share, in particular, a front optic. Even then the beam path is configured such that the illumination by the illumination radiation and the collection of the backscattered measurement radiation have independent, e.g. different, numerical apertures. Thus the illumination is provided with a numerical aperture which illuminates an axially large area, with the result that the collected measurement radiation originates from a comparatively large depth area and consequently the OCT principle obtains an image over a large depth area. The numerical aperture of the collection of the measurement radiation, thus of the imaging of an object area, is set independently of the numerical aperture of the illumination, e.g. may be larger. A high lateral resolution is thereby combined with a large illuminated depth area.

The detector is a two-dimensional detector comprising pixels. In embodiments, the pixel number lies between 4 and 100 pixels per direction and per hole of the multi-hole diaphragm, in another example between 5 pixels and 40 pixels. Such pixel numbers proved to be advantageous for sampling each object spot both with respect to resolution and with respect to signal-to-noise ratio and possible image error corrections.

The aberrations that the eye generates are particularly important for image error correction. Since the invention decouples the numerical apertures of illumination and detection, some embodiments carry out the detection, i.e. the imaging of the object area on the retina, at numerical apertures, at which aberrations of the eye might become a problem. The spatial resolution at which the 2D detector detects each object spot makes it possible, as explained below, to correct the aberrations in particular if the detector is arranged in a conjugated pupil plane of the imaging beam path. If the detector does not lie in a pupil plane, an aberration correction is likewise possible if the detected signal is converted to relate to a pupil plane, as is known for holograms in the state of the art.

In the object plane and the (intermediate) image planes of a beam path the image information is pure location information. Imaged structures can be noted in (intermediate) image planes. There they take the form of intensity differences. In pupil planes the image information is pure angle information. Here, the angles of the incident beams encode the image information. This has the known effect that a cross-sectional alteration in a pupil influences exclusively the image brightness, but not the image size. For this reason the human eye iris lies in the pupil plane, with the result that the human eye adapts with respect to brightness by narrowing or widening of the iris. When the plane of the pupil of the eye is discussed in this description, the iris plane is meant. An imaging beam path images an object from the object plane onto an image in the image plane (e.g. the location of a detector). Because of the laws of imaging, there always exists a pupil between for example the object plane and an intermediate image plane. Similarly, there always exists an intermediate image plane between two pupil planes. Likewise, in this description, planes which are located between the plane of the pupil of the eye and the detector are called conjugated pupil planes, as they are conjugated to the plane of the pupil of the eye, predetermined by the optically imaging elements. Where the retina is named as the object here, that is not intended to limit the invention. Other structures of the eye can equally be imaged as object.

The features of the optical coherence tomography described herein can be used alone or in different combinations for various embodiments. Where the following embodiment examples describe particular combinations of features, the invention is not limited to such combinations.

The invention achieves a combination of the advantages of a confocal scanning system with the advantages of a spatially sampling detector. The confocal principle of a scanning system supresses scattered radiation very effectively, whereby an improved signal-to-noise ratio is achieved. At the same time the lateral resolution can be increased by enlarging the aperture on the eye. The invention provides that the numerical aperture of the illumination is decoupled from the numerical aperture of the detection. This achieves a high lateral resolution without impairing the detectable depth area. The design aims contradictions in the state of the art (high lateral resolution requires high NA, large detectable depth area requires small NA) are thus both achieved.

Some embodiments of the invention use a confocal multi-hole diaphragm. In this description the term "confocal" not only relates to a diaphragm which lies exactly in an (intermediate image) plane conjugated to the object plane, but also encompasses an arrangement of the diaphragm which lies within a certain margin of error in front of or behind an intermediate image plane. If the confocal diaphragm does not lie exactly in the intermediate image plane, but lies close to the intermediate image plane, then, although a scattered light suppression may possibly be reduced, the function as confocal diaphragm which defines the object field from which the measurement radiation is collected is still fulfilled. The diaphragm is in or close to an intermediate image plane as long as it is in a distance from the intermediate image plane not more than three times the imaging depth; a distance of not more than one times the imaging depth is for example, preferred. The imaging depth is also called "depth of focus" in the literature and defines an axial area in the image space, i.e. on the intermediate image plane of an optical system in which a sufficiently sharp image forms in a detection plane. Diffraction spots are detected as a dot in the area of the depth of focus. The area in the object space conjugated to the depth of focus is the depth of field. The depth of field is a measure of the extent of the sharp area in the object space and is given by $\lambda/(NAo)^2$, wherein NAo denotes the numerical aperture in the object space. The depth of focus on the intermediate image plane results, analogously to the depth of field, from the numerical aperture by $\lambda/(NAz)^2$; NAz is the numerical aperture in the intermediate image plane, which is calculated e.g. from NAo by of the imaging scale. In the above calculations, the maximum wavelength of the measurement radiation can be used as wavelength in the intermediate image plane.

In ophthalmological applications, the invention has the advantage that higher light intensities can be radiated into the human eye, because they are distributed onto larger cross sections of the anterior chamber of the eye. To obtain that advantage the illumination beam path comprises structure which illuminates the retina with a multi-spot pattern and places the pupil of the illumination within the eye and, in some example embodiments, illuminates the full diameter of the iris (approx. 4.2 mm) in the eye. Some example embodiments place the effective position of the illumination pupil in the plane of the iris. This can be done by using a field lens, alternatively also by a corresponding layout of the optical system between the eye and by a multi-spot diaphragm of the illumination beam path.

A pupil position outside the eye would have the result that the bundle of illumination beams does not irradiate through the iris on the optical axis for all spots. A small angle between illumination and detection, which can lead to vignetting effects over the measurement depth of the retina, thereby results. These effects can be disadvantageous for highly precise applications.

The invention generates several illumination spots on the object, e.g. the retina, from a homogeneous plane illumination wavefront without losses and at the same time utilizes all pixels on the 2D detector.

Various principles come into consideration for the detection. Some embodiments use a single detector or a balanced detection or an off-axis detection.

It is understood that the features mentioned above and those yet to be explained in the following are applicable not only in the stated combinations, but also in other combinations or singly, without departing from the scope of the present invention.

BRIEF DESCRIPTION OF THE DRAWINGS

The invention is explained in even more detail below by way of example with reference to the attached drawings, which also disclose features essential to the invention. There are shown in.

DETAILED DESCRIPTION

Figure 1:
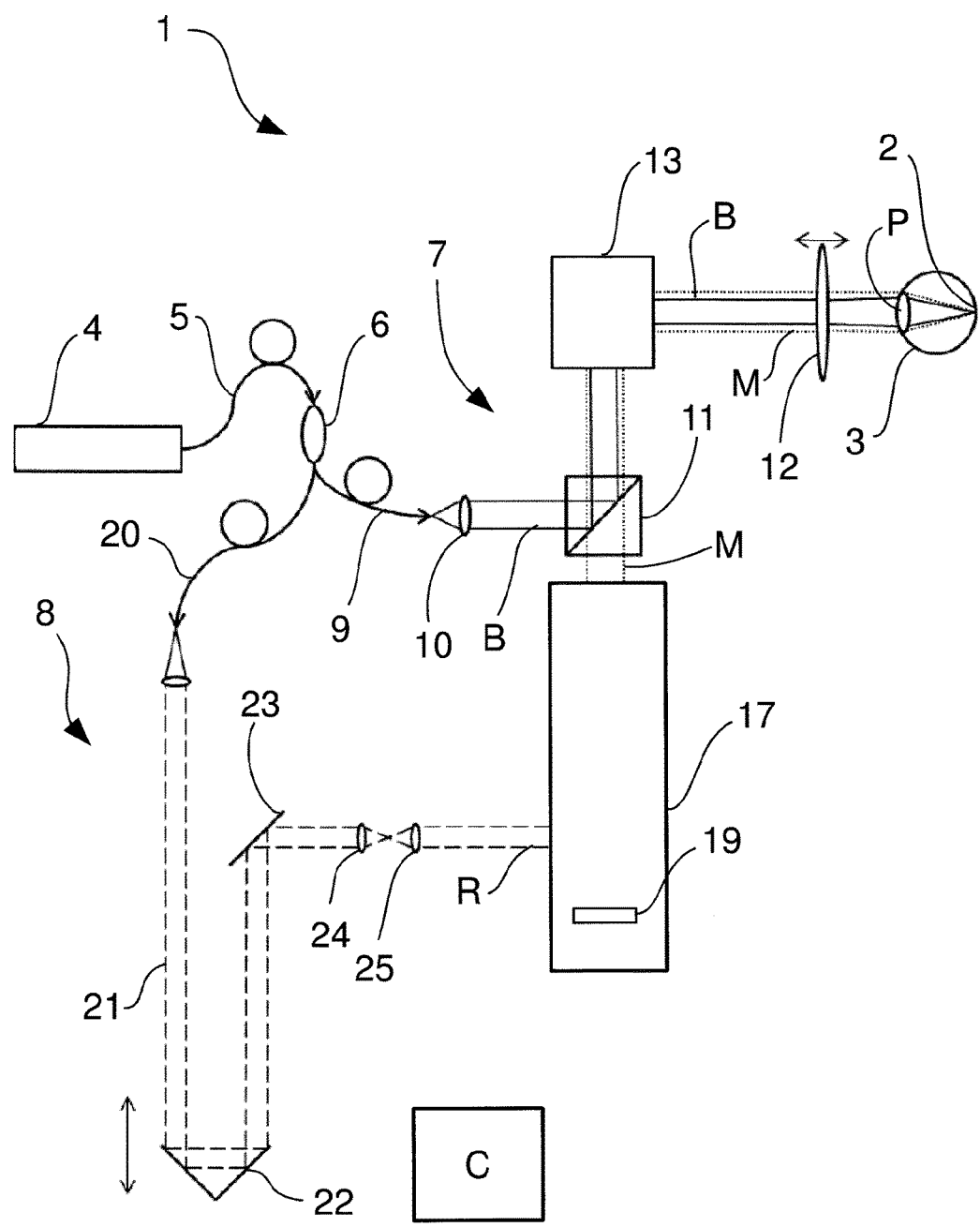
FIG. 1 a schematic representation of an optical coherence tomograph (OCT) in a first embodiment, FIG. 2 a schematic representation of an OCT in a second embodiment, FIGS. 3a-d schematic representations of different variants of the detection beam path of the OCT of the first and second embodiments, FIG. 4 representations to illustrate an aberration correction which can be used in an OCT of FIG. 1 or of FIG. 2, FIG. 5 a top view of a detector which can be used in an OCT of FIG. 1 or of FIG. 2, FIG. 6 a representation to illustrate a depth correction which can be applied in an OCT of FIG. 1 or of FIG. 2, FIG. 7 signal intensities of different channels of a detector of an OCT according to one of FIG. 1 or 2, FIG. 8 a representation similar to that of FIG. 7, FIG. 9 a schematic representation to illustrate the scanning principle in an OCT according to one of FIG. 1 or 2, and FIGS. 10 and 11 schematic representations similar to that of FIG. 9 to illustrate the generation of a three-dimensional image.

FIG. 1 shows an OCT 1 which captures three-dimensional images of a retina 2 of an eye 3. Source radiation of a radiation source 4 which is tunable with respect to its wavelength, for example of a corresponding laser, is coupled into a fiber 5. The source radiation is for example of infrared wavelength. In the following description this wavelength range is also called "light". All radiation of the electromagnetic spectrum which satisfies the optical laws is to be subsumed under this term.

The fiber 5 feeds a splitter 6, which splits the source radiation into a measurement arm 7 and a reference arm 8. In the measurement arm 7 a fiber 9 follows the splitter 6, and the illumination radiation B emerging at the fiber end is guided to a beam splitter 11 by means way of an illumination optical system 10. From there it reaches a front optics 12, which bundles the illumination radiation B into a focus which lies on the retina 2 of the eye 3. The illumination optical system 10 and the front optics 12 set, among other things, numerical aperture NA with which the eye 3 is illuminated. A scanner 13 which deflects the focus on the retina 2 biaxial and perpendicular to the direction of incidence, i.e. lateral, is located between the beam splitter 11 and the front optics 12. The directions of this deflection may be denoted x and y in the following. A z position of the focus can be set by adjustment of the front optics 12. This is indicated schematically by a double arrow in FIG. 1.

The illumination radiation in the illumination focus on the retina 2 is backscattered from different depths within a depth of field range. The depth of field range is defined by numerical aperture NA, which is determined by the front optics 12 and the illumination optical system 10 as well as the optical properties of the eye 3.

Backscattered radiation is collected by the front optics 12 as measurement radiation M. To distinguish between the incident illumination radiation B and the backscattered measurement radiation M collected by the front optics 12, these are entered differently in FIG. 1. In the figure the illumination radiation is shown with continuous lines, the measurement radiation M with dotted lines. The measurement radiation collected by the front optics 12 is guided to the scanner 13. It is descanned here, with the result that after the scanner 13 the measurement radiation M is a stationary beam.

Collection of the measurement radiation M is, in fact, imaging of the retina 2. The beam splitter 11 separates the measurement radiation M from the illumination radiation B and guides the isolated measurement radiation 14 to a detector device 17. The detector device 17 will be explained in more detail later with reference to FIG. 3. It has, among other things, an optical system which, together with the front optics 12 and the optical properties of the eye 3, defines numerical aperture NA of the imaging of the retina 2. In this way, illumination and detection have independent numerical apertures. Numerical aperture of the illumination is defined by the illumination optical system 10 and the front optics 12, numerical aperture of the detection is defined by the front optics 12 and the detector device 17.

Reference radiation R from the reference arm 8 is also coupled in towards the detector device 17. The reference arm comprises a fiber 20 after the splitter 6. In the embodiment shown in FIG. 1 the reference arm 8 comprises a pathlength adjusting device 21, which serves to set the optical length of the reference arm 8 suitably relative to the position of the retina 2 of the eye 3. In an embodiment of the pathlength adjusting device 21 couples out the radiation from the fiber 20 and guides the radiation through a retroreflector 22, the position of which can be adjusted, as indicated by the double arrow in FIG. 1. A further deflecting mirror 23 and optical systems 24, 25 guide the reference radiation R to the detector device 17, which guides the reference radiation R superimposed with the measurement radiation M to a 2D detector 19.

The pathlength adjusting device 21 is provided as a free beam path in FIG. 1. This is optional, as is the use of a retroreflector 22. In the state of the art various measures are known for adjusting the optical pathlength of a beam.

The interference between reference radiation R and measurement radiation M is implemented to generate an image by optical coherence tomography. As the wavelength of the source radiation is tuned, the Fourier domain principle is used for OCT image generation, which is known to persons skilled in the art.

For image generation, OCT 1 comprises a control device C which receives a signal about the wavelength tuning and the measurement signals of the detector 19. Optionally, the control device C controls the wavelength tuning of the radiation source 4 and, therefore, knows the wavelength currently propagating in the system and can thus process the measurement signals accordingly. The detector 19 receives measurement radiation M from an object field on the retina 2, which field is defined by a diaphragm in the detector device 17 (see FIG. 3). The detector 19 comprises pixels and is matched in terms of its size to this diaphragm and samples the intensity distribution in a spatially resolved manner with the pixels. In some embodiments the detector 19 lies in an image plane, i.e. in a plane which is, in the imaging carried out by the front optics 12, detector optical system 14 and the further optical elements located in-between, conjugated to the plane of the retina 2. Then, the individual pixels directly provide the location information in the object field. In other embodiments the detector 19 lies in a conjugated pupil plane which is conjugated to the plane in which the pupil P of the eye 3 lies. Then, the pixels detect the intensity distribution in the pupil plane and thus the angle information. This can also be used for image reconstruction, as will be explained below.

For the invention it is important that the scanner 13 shifts the object field in the retina 2 and acts not only on the illumination radiation B, but also on the collection of the measurement beams M. A partial image of the retina thus forms at each position of the scanner 13. These partial images are, as will be explained below, combined to form a total image which has a much higher resolution than those known from widefield OCT.

In the embodiment of FIG. 1 the detector device 17 combines the measurement radiation M from the measurement arm 7 and the reference radiation R from the reference arm 8. The detector 19 detects the pattern of interference between measurement radiation M and reference radiation R. To generate such an interference, in particular the properties of the radiation source 4 and the path length adaptation, are known in the art of optical coherence tomography.

The complex amplitudes of the measurement radiation and of the reference radiation can be written as:

$$U_{sample} = u_s * e^{i\varphi_s} \text{ and}$$

$$U_{reference} = u_r * e^{i\varphi_r},$$

if $u_s$ and $u_r$ denote the amplitudes and $\varphi_s$ and $\varphi_r$ denote the phases of the signals in the two arms (the subscripts "sample" and "s" refer to the measurement arm, the subscripts "reference" and "r" refer to the reference arm).

The detector detects a signal $I_1$ and, in the case of a "balanced detection", which will be discussed later, also a signal $I_2$:

$$I_1 = |U_{sample} + U_{reference}|^2 = |U_{sample}|^2 + |U_{reference}|^2 + 2Re\{U_{sample}*U_{reference}\}$$

$$I_2 = |U_{sample} + U_{reference} * e^{i\pi}|^2 = |U_{sample}|^2 + |U_{reference}|^2 + 2Re\{U_{sample}*U_{reference}*e^{-i\pi}\}.$$

The amplitude of the interference signal is modulated to common-mode portions $|U_{sample}|^2$ and $|U_{reference}|^2$ is filtered out by corresponding data analysis or a balanced detection or an off-axis detection.

Figure 2:
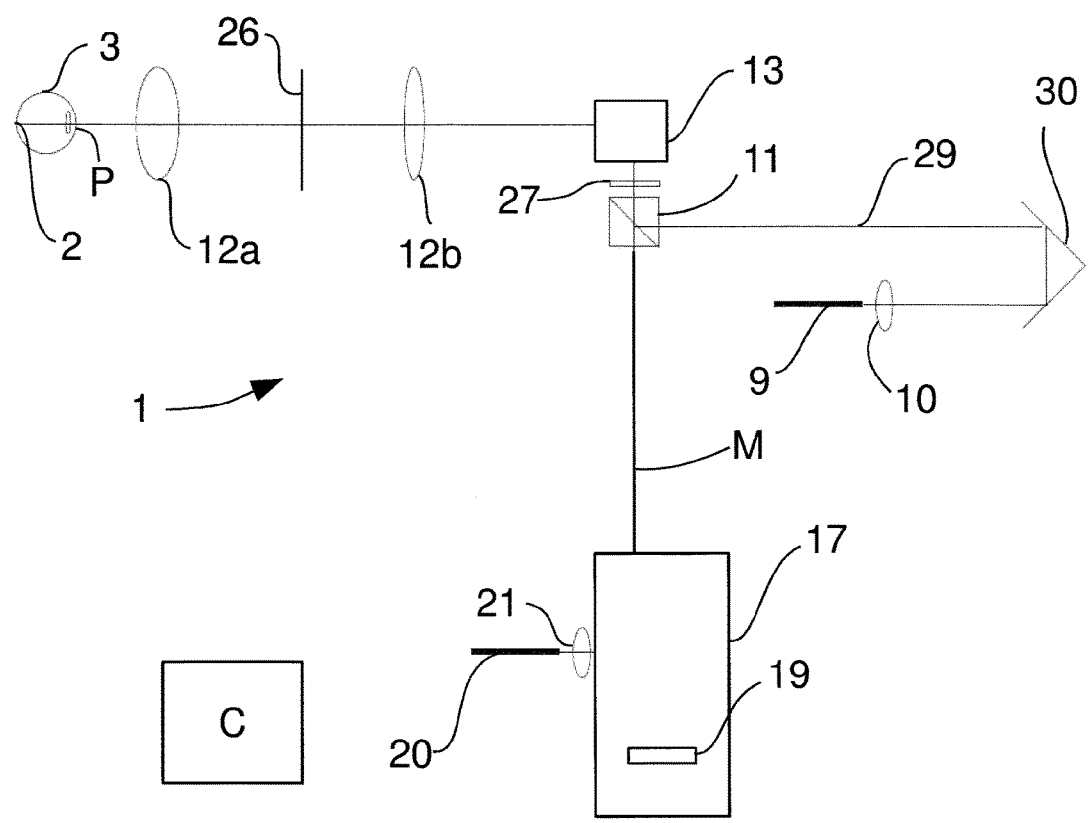

FIG. 2 shows a further embodiment for the OCT 1, in which the pathlength adjusting device is arranged not in the reference arm 8, but in the measurement arm 7. Pathlength adjusting device 29 is located after the fiber 9 and the illumination optical system 10, again purely by way of example by use of a movable retroreflector 30. The embodiment of FIG. 2 shows that it makes no difference whether the pathlength adjusting device lies in the reference arm 8 or in the measurement arm 7. It is also possible to provide a pathlength adjusting device in both arms. The only important thing is that the interference state between the reference radiation R from the reference arm 8 and the measurement radiation M can be matched to the current measurement task, i.e. the actual position of the object to be measured, in the embodiment examples described herein the retina 2 of the eye 3.

In FIG. 2 an embodiment is shown in which the front optics 12 is formed in two parts by two imaging elements 12a and 12b. This is optional.

For applications at the eye 3 specifications for a maximum allowable illumination intensity on the cornea are to be obyed. If the illuminated field is enlarged, more illumination radiation energy can be coupled in onto the eye 3, without exceeding a threshold for the illumination intensity density. In ophthalmological applications and in the infrared wavelength of usual OCTs, a maximum luminance of approximately 1 mW/mm$^2$ must not be exceeded in the anterior chamber of the eye. If an eye pupil diameter of 4.5 mm is illuminated homogeneously, a total of approximately 16 mW would be allowable, thus. In order not to allow the depth-scannable area to become too small, however, the whole pupil P of the eye 3 is not utilized for the illumination. Instead, an NA of approximately 0.035 (or a pupil diameter of 1.2 mm) is for example used as upper limit for proper depth detection.

For the tissue of the retina the maximum allowable power is at 1.5 mW for spots smaller than 1.5 mrad and at a wavelength of 1060 nm. This has the result that the 16 mW allowable with respect to the pupil have to be distributed over an angle of 15 mrad in at least one direction, in order not to exceed the maximum value of the retina 2. Then the whole signal intensity would have been maximized, but at the expense of the image contrast, because scattered light is to be expected for such high intensity radiation under normal widefield illumination conditions.

Figure 3A:
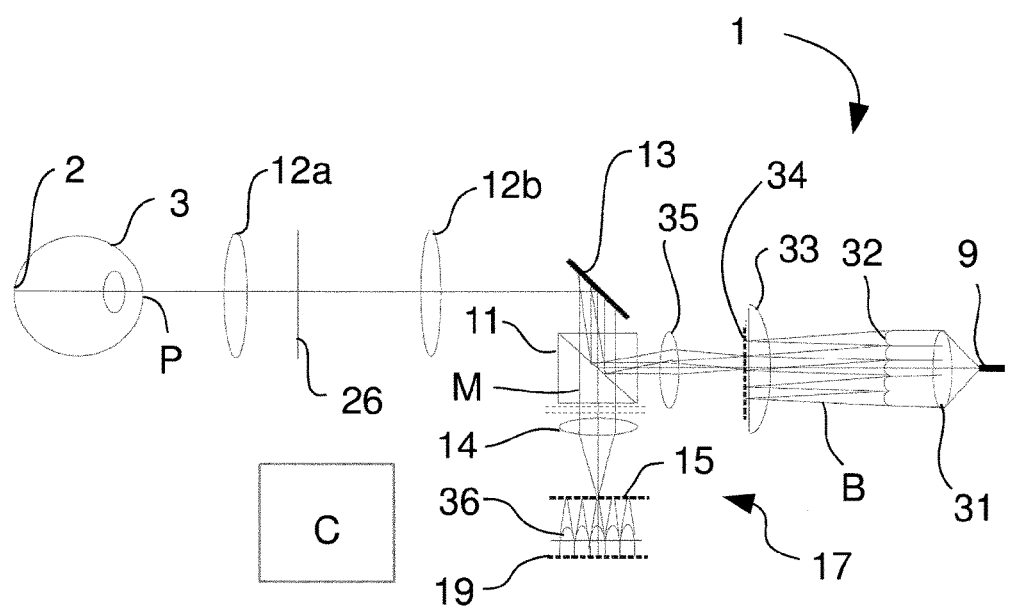
Figure 3B:
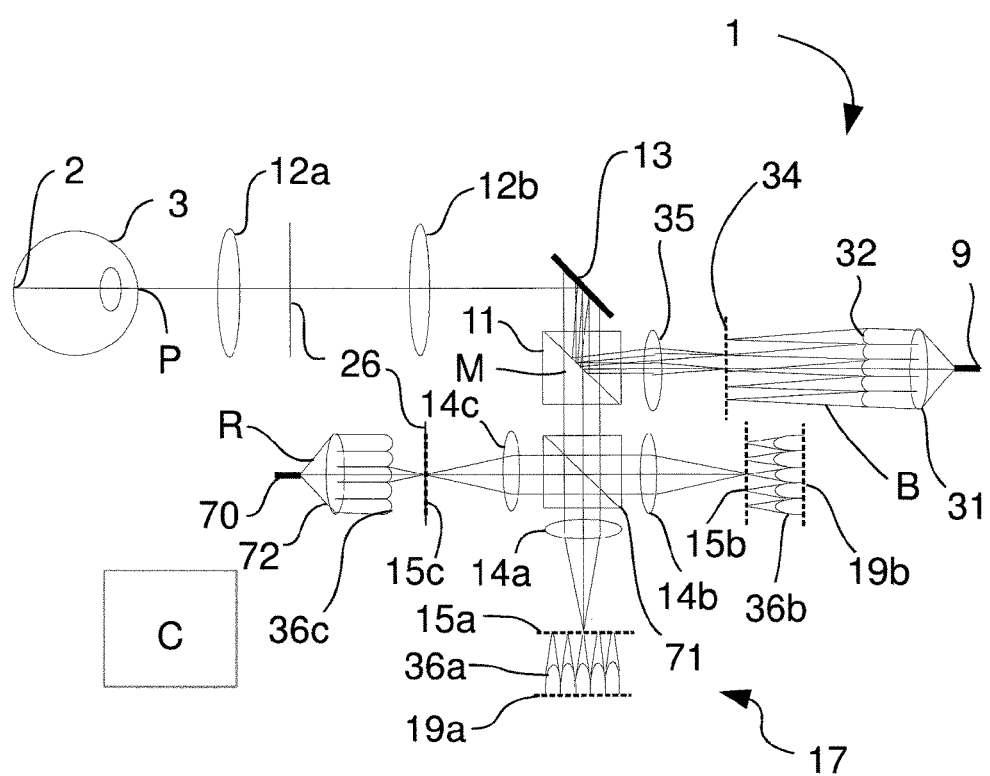
Figure 3C:
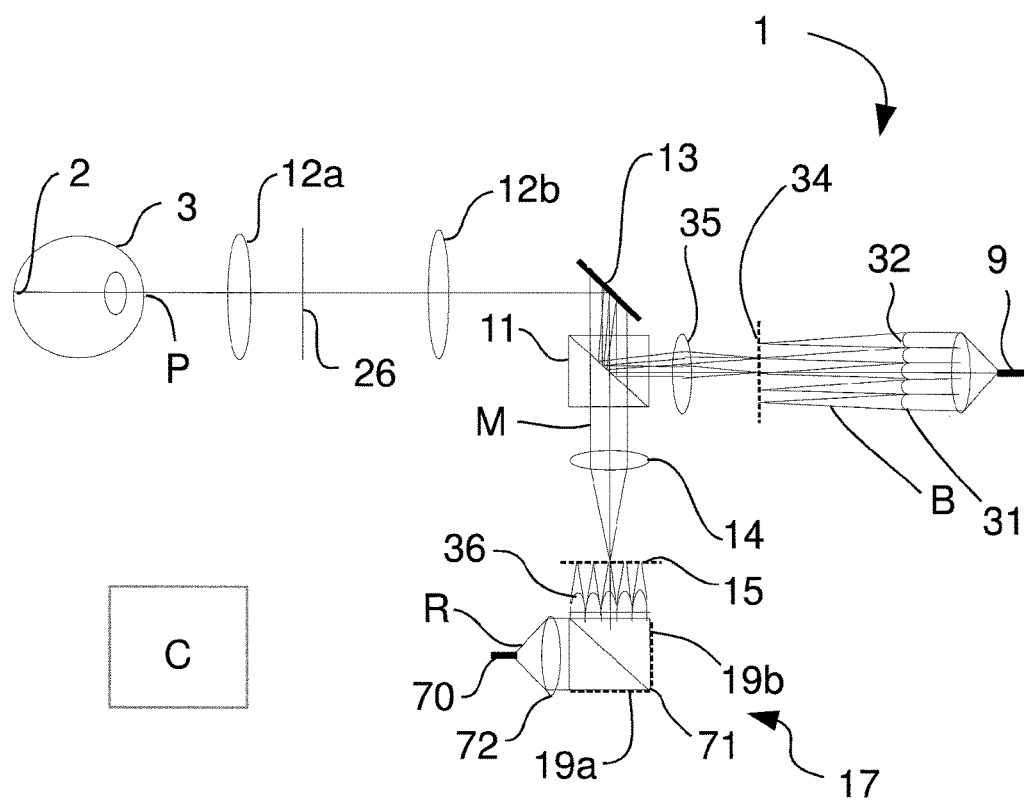
Figure 3D:
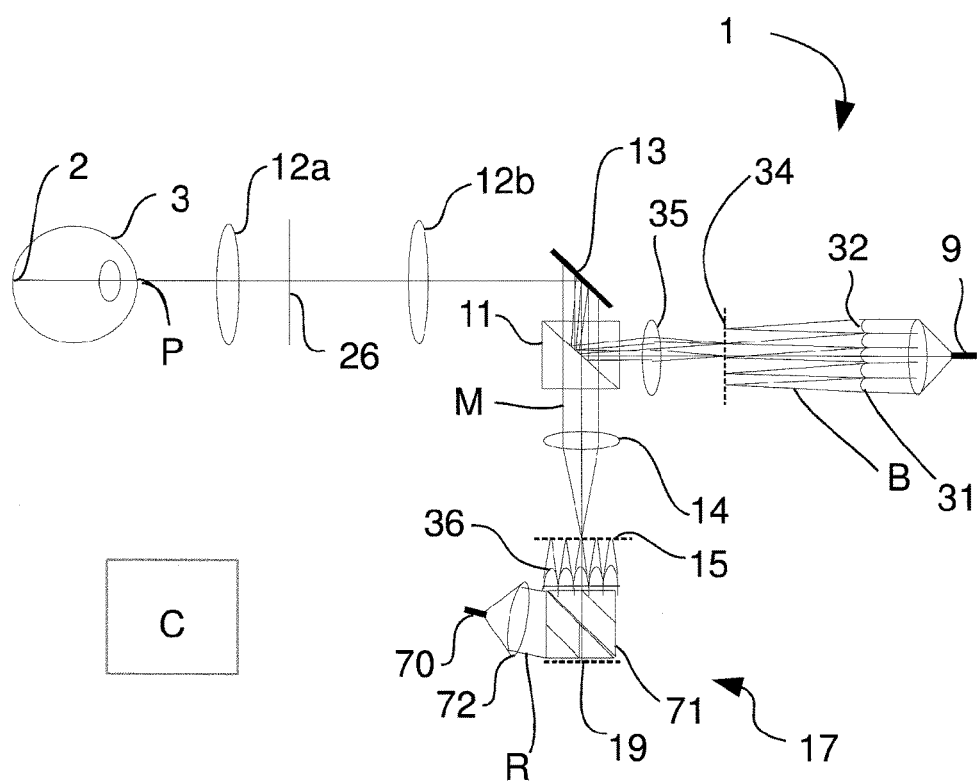

OCT 1 resolves this conflict of aims by illuminating and detecting the retina simultaneously at several spots spaced apart from each other. The problem of scattered light is minimized by the spacing of the spots. FIGS. 3a-d schematically show the elements of OCT 1 which are relevant for this, wherein all components which relate to the generation and coupling-in of the reference radiation R have been omitted for the sake of simplicity. Elements of FIGS. 3a-d which correspond to elements which have already been explained with reference to the previous figures are provided with the same reference signs, with the result that repetition of their description can be dispensed with. In the representation of FIG. 3a the coupling-in of the reference radiation R takes place at the site of the dotted double line. FIGS. 3b-d show different variants for implementing the coupling-in and also the detection.

Illumination and detection are done in accordance with a multi-spot principle in the OCT of FIGS. 1 and 2, as FIGS. 3a-d show. However, this does not apply to the reference beam path 8, which does not guide radiation in several spots. The guiding of the reference radiation is not shown in FIG. 3. The reference radiation is coupled in at the site of the dotted double line, thus, in imaging direction of FIG. 3a, after the beam splitter 11 and before the optical system 14. This coupling-in is not shown in FIG. 3a for the sake of simplicity. Optical system 14 is optical system, explained with reference to FIG. 1, of the detector device 17, which together with the front optics 12 and the optical properties of the eye 3 defines numerical aperture NA of imaging of the retina 2. The optical system 14 constitutes, thus, a detection optical system 14.

Detection optical system 14 focuses the measurement radiation M into an intermediate image plane, in which a diaphragm 15 is located. Diaphragm 15 defines the size of the object field, from which measurement radiation M is collected at the retina 2. Taking into account the imaging scale of detection optical system 14, front optics 12 and eye 3, the size of the diaphragm 15 corresponds exactly to the size of the object field on the retina 2, from which measurement radiation M is collected.

The diaphragm 15, as will be explained below, is formed as a multi-hole diaphragm which, together with subsequent components, to be explained in even more detail later, images a plurality of object spots on the retina onto a corresponding number of detector spots on detector 19. Detector is designed such that each detector spot, in one direction, is covered 4 to 100 pixels, in other examples from 5 to 50 or 5 to 40 pixels. The detector thus samples each spot with respect to its intensity distribution using individual detector areas. The significance of this sampling establishing holographic OCT will be discussed below.

According to FIGS. 3a-d illumination radiation B provided at the end of the fiber 9 is distributed onto spots and coupled in over the whole usable pupil P (diameter 4.5 mm) of the eye 3. In this way, both the upper power limits at the cornea of the eye 3 and the upper power limits at the retina 2 of the eye are complied with. If the spots are formed such that they have a minimum spacing of 2 mm on the retina 2 (in general terms: a spacing which approximately corresponds to the detectable depth area of the OCT), photons scattered multiple times are suppressed as effectively as in the case of a confocal OCT, which would deflect an individual spot. This solves the problem of scattered light.

Illumination radiation B coupled out of fiber 9 is collimated by collimator lens 31 and then bundled onto multi-hole diaphragm 34 using multi-lens array 32 and field lens 33. Multi-hole diaphragm 34 specifies pattern, spacing and size of the illumination spots on the retina 2, as it lies in a plane which is, because of the subsequent optical system 35, 12a, 12b, conjugated to the object plane on the retina 2. Optical systems are for example, configured such that both the beam splitter 11 and the scanner 13 lie close to a pupil of illumination beam path. Optional field lens 33 in front of the multi-hole diaphragm 34 ensures that in the plane of pupil P of the eye 3 the radiation is distributed uniformly over the whole pupil P, i.e. over the diameter of 4.5 mm, with the result that no points exist there in which the maximum radiation intensity might be exceeded.

Measurement radiation M backscattered on the retina 2 is imaged onto the detector 19 by way of the front optics comprising optical systems 12a, 12b via the intermediate image plane 26 and the scanner 13 as well as the beam splitter 11, which both lie close to or in a conjugated pupil plane which is conjugated to the plane of pupil P of the eye 3; of course after reference radiation has been coupled-in by the detector optical system 14 (in the section between the dotted double lines). The multi-hole diaphragm 15 in FIG. 3 realises the diaphragm described with reference to FIG. 1. A downstream multi-lens array 36 images the measurement radiation M from the individual diaphragm openings of the multi-hole diaphragm 15 onto the detector 19. The multi-lens array 36 ensures that the measurement radiation M which is incident through the individual diaphragm openings of the multi-hole diaphragm 15 no longer mixes before it reaches the respectively allocated pixels of the detector 19. Each hole of the multi-hole diaphragm 36 illuminates a group of several pixels of the detector 19 with each group forming one detector area.

FIGS. 3b-d show some options how to couple-in reference radiation R. Reference radiation R originates by way of example from an end of an optical fiber 70 which forms the end of the additional pathlength through which the reference radiation R is sent. A free beam guiding is equally possible for all embodiments.

With reference to FIG. 3b the reference radiation is superimposed with the measurement radiation to perform a balanced detection. Balanced detection is also done in the embodiment of FIG. 3c and an off-axis detection is carried out in the embodiment of FIG. 3d.

As FIG. 3b shows, the measurement radiation is superimposed, by application of a beam splitter 71, with the reference radiation R which is guided by optical fiber 70 and in advance is distributed, using a lens 72 and a multi-lens array 36c, into a plurality of spots, wherein the focal plane of the multi-lens array 36c lies in an intermediate image plane 26. A multi-hole diaphragm 15c can optionally lie there. Optical system 14c collimates the radiation and guides it to beam superimposer 71. The latter superimposes the measurement radiation M with the reference radiation R and guides the radiation to two detectors 19a, 19b, upstream of each of which a optical system 14a, 14b, a multi-hole diaphragm 15a, 15b and a multi-lens array 36a, 36b are arranged. The multi-lens arrays 36a, 36b in front of the detectors 19a, 19b and the multi-lens array 36c are matched to each other and to the multi-lens array 32 as well as the multi-hole diaphragm 34 of the illumination beam path.

The embodiment represented in FIG. 3b can be used for all multi-spot systems of the invention which are equipped with a balanced detection. The measurement radiation M is superimposed in the detection beam path close to the pupil coherently with the reference radiation R and then imaged into and detected in two independent beam paths with the two detectors 19a, 19b. The multi-hole diaphragms 15a, 15b are conjugated to the multi-hole diaphragm 34 of the illumination beam path. The measurement radiation M which passes through the multi-hole diaphragm 15a or 15b is collimated by the multi-lens array 36a or 36b and recorded with the detector 19a or 19b.

If the illumination beam path utilizes a pupil in the eye with a diameter of approx. 1.2 mm and the detection beam path uses a pupil with a diameter of 4.5 mm, the microlenses of the multi-lens arrays 36a-b in the detection have a focal length that is 4.5/1.2=3.75 times smaller than the microlenses of the multi-lens array 32. The angular spectrum of the radiation at the area detectors 19a, 19b of the various spots then precisely fills the sensor, without there being an overlap or gaps. The imaging scale between the image plane of the retina 2 and the multi-hole diaphragms 15a, 15b of the detection is chosen such that a desired number of pixels covers and detects each individual spot which is generated by one microlens of multi-lens array 36a, 36b, for example ten pixels per spot are used. The detection is done close to the pupil, i.e. detectors 19a, 19b lie in a plane which is conjugated to pupil plane P. The multi-hole diaphragms 15a, 15b on the other hand lie in intermediate image plane 26 conjugated to image plane (plane of the retina 2).

To have coherent detection, each bundle of measurement beams is superimposed with a bundle of reference beams at an identical aperture. This is achieved by collimating reference radiation R, which emerges from optical fiber 70, with lens 72 and focusing it by the multi-lens array 36c into intermediate image plane 26. A reference wave forms there in form of a multi-spot pattern which is imaged onto multi-hole diaphragms 15a, 15b with the aid of the further lens 14c as well as lenses 14a, 14b in the superimposed beam path section of reference radiation R and measurement radiation M. Lens 14c for example forms with the lenses 14a and 14b a 4f type arrangement.

If each spot illuminates a field with a diameter of approximately 20 μm on the retina 2 and these spots have a spacing of approx. 2 mm, the multi-lens arrays 36a, 36b utilize comparatively small effective field angles. It is then not necessary for the detectors 19a, 19b to be strictly in the focal planes of the microlenses of the multi-lens arrays 36a, 36b, rather they can also be at a greater distance. Phase variances which can may occur over the area detectors can be numerically compensated for after the coherent detection.

If distance between microlenses of the multi-lens array 36a, 36b and the detector 19a, 19b can be larger, a particularly simple detection arrangement for the balanced detection is possible, as FIG. 3c shows. It is sufficient then to collimate the reference radiation R with the lens 72 only such that the detectors 19a, 19b are illuminated in 2D. Only a single multi-hole diaphragm 15, with one multi-lens array 36, which is upstream of the beam combiner 71 is needed then.

FIG. 3d shows an off-axis detection in which there is sufficient space between the multi-lens array 36 of the detection beam path 17 and the detector 19 to superimpose with measurement radiation and reference radiation R. In this case too, if the spacing between multi-lens array 36 and detector 19 is larger than the focal length of the microlenses of the multi-lens array 36 prescribe, phase variations forming over the detector 19 can be numerically compensated when processing data.

For the principle of off-axis detection it is generally preferred, for example, to implement the multi-lens array 36 using anamorphic cylindrical lenses on the front and back side of a plane-parallel substrate layer plate of certain thickness. This arrangement, together with a rectangular arrangement of the microlenses in the multi-lens array 36, also makes it possible to illuminate the camera pixels of the detector 19 without losses in off-axis, even if more pixels (e.g. 2-3 times) are needed in the off-axis direction for imaging with the same aperture values.

In off-axis detection the angle relative to the optical axis is chosen according to various detection parameters. The smaller the angle, the larger the spacing between multi-lens array 36 and detector 19. Spacings that are too large and angles that are too small have the result that the phase variances forming can no longer be numerically corrected sufficiently well. An angle that is too large on the other hand has the result that the coherence of the superimposition may be lost. The use of a TIRF prism as beam combiner 71 represents a particularly good compromise. This prism is constituted by two glass prisms with a small air gap in-between, which is drawn in schematically in FIG. 3*d* for the beam superimposer 71. The glass prisms are dimensioned such that the measurement radiation M is incident on the air gap at an angle of 45° and can still be transmitted, whereas the reference radiation R, because of the angular offset, is incident at more than 45° and totally reflected, thus reaches the detector 19 in full. The angle of 45° is only one example. The decisive thing is that, for the measurement beam, the limit angle for total internal reflection is not exceeded, with the result that the measurement radiation M can pass through the TIRF prism, while the light from the reference is incident on the glass-air interface at a larger angle than the limit angle, with the result that the reference light R is reflected and therefore is guided to the detector. The limit angle for prisms (with a refractive index of n(prism)>1) with an air gap (with a refractive index of n(air)=1) is theta.limit=arcsin (n(air)/n(prism)). At the same time the angle of the reference light R on the sensor must, naturally, correspond to the angle for an off-axis detection. This results from the width of the pixels and the number of pixels, over which a phase amplitude of 2*pi is distributed.

As already explained above, the image information is present in a pupil of the beam path in the form of angle information, and the intensity distribution in the pupil is generally entirely uniform. It is therefore a preferred in an example embodiment to arrange optical elements which are to act equally on all structures to be imaged in a pupil. Such elements are, for example, the scanner 13 and the beam splitter 11. However, it is not mandatory to arrange these elements entirely and exclusively in a conjugated pupil plane. In the embodiment of FIG. 3 it is sufficient for example to arrange these elements such that the beams which belong to neighbouring holes of the multi-hole diaphragm 34 are already superimposed. This is the case when the corresponding edge beams intersect.

Similarly, an embodiment is preferred for example, in which lenses or other elements which can generate reflections, are arranged where possible outside a conjugated pupil plane. Here too, this provision is not to be understood as imperative. It is sufficient to arrange such elements in areas in which bundles of beams of neighbouring holes of the multi-hole diaphragm 34 do not yet start to overlap, thus their edge beams have not yet intersected. In the case of the embodiment of FIG. 4 the term "close to the pupil" or "far away from the pupil" thus relates to location along the optical axis at which edge beams of neighbouring holes of the multi-hole diaphragm 34 start/end to intersect.

The scanner 13 of OCT 1 of FIGS. 1 to 3 is located for example, in or close to a pupil plane of the detection beam path as well as also of the illumination beam path. This pupil plane is conjugated to the plane of the pupil P of the eye 3.

The front optics 12 optionally comprises, as shown by way of example for the embodiment of FIG. 2, opticals 12*a* and 12*b* which, together, form a 4f type optical system. Opticals 12*a* is then an ophthalmoscopic lens and opticals 12*b* is a scan lens. This 4f type optical system images pupil P of eye 3 to pupil plane which is conjugated to the plane of pupil P and in which the scanner 13 lies. It is not necessary to place the scanner 13 exactly in this conjugated pupil plane, but has advantages. An intermediate image plane 26 is located between the plane of pupil P of the eye 3 and pupil plane conjugated thereto. The beam splitter 11 is located, because of its proximity to the scanner 13, likewise close to conjugated pupil plane. It is also possible to place the beam splitter 11 in this conjugated pupil plane if the scanner 13 is moved out of conjugated pupil plane.

In an embodiment the beam splitter 11 is formed by a polarizing beam splitter. This is then preceded in the imaging direction by a lambda/4 plate 27 (cf. FIG. 2). This embodiment will be discussed in the following.

The detector optical system is preferably, for example, likewise formed as a 4f type optical system. It provides a further intermediate image plane 26 in which the diaphragm 15 lies. The intermediate image plane 26 is conjugated to the object plane in which the retina 2 to be imaged lies.

Diaphragm 15, 15*a*, 15*b* has two functions in all embodiments. Firstly it suppresses scattered light, whereby the contrast on the detector device 17 is improved. The diaphragm acts, in this respect, similarly to a confocal diaphragm for confocally sampling OCT. The detector 19 is positioned, because of the detector optical system, for example in a plane which is conjugated to the pupil plane of the eye, or close to this plane. This arrangement is advantageous, but not mandatory. It has the advantage that the phase function of the electromagnetic field can be sampled simply. The maximum spatial frequency in the plane of the detector 19 is predefined by the object field size on the retina 2 and thus ultimately by the size of the diaphragm 15 in the intermediate image plane 26. The diaphragm 15 thus ensures, on the other hand, a particularly favourable signal generation and processing.

Figure 5:
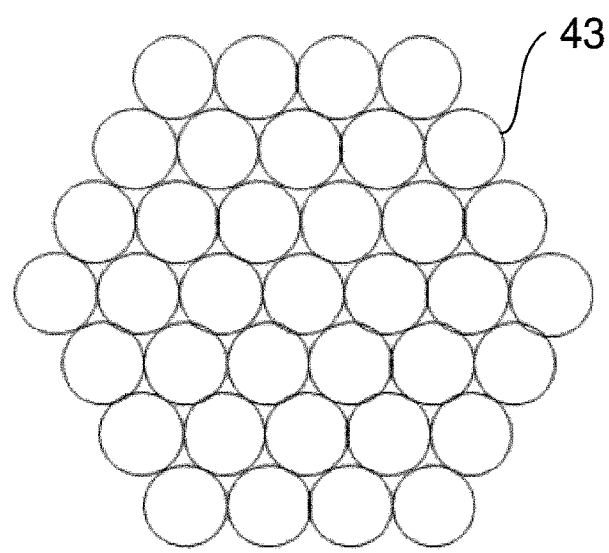

In all embodiments of the OCT the detector has, per hole of the multi-hole diaphragm 15, a pixel group of, for example, 4 to 100 pixels, in another example—5 to 50, in a further example 5 to 40 pixels in each direction. FIG. 5 shows, in a top view of the detector pixels 43, that the arrangement of the pixels 43 need not necessarily be rectangular, but a hexagonal arrangement of the pixels 43 also comes into consideration. The pixel pattern can thus be chosen freely.

In the state of the art, holoscopic OCT systems are known which have detectors with 100 to 4000 pixels per direction. These pixel numbers are deliberately not used here. The number of pixels is linked to the necessary illumination brightness, the measurement speed and the suppression of multiple scattering.

In an example embodiment of the OCT 1 aberrations are corrected. The pixels of the detector 19 are also referred to as channels in the following. The measurement signal is distributed over these several channels. If the detector 19, according to an example embodiment, lies in a conjugated pupil plane, each channel of the detector contains measurement radiation M from various angles which was scattered inside the retina 2. The spatial resolution of the detector 19 makes it possible to detect the distribution of the measurement radiation in the pupil P for each spot. The following explanation refers to only one of these spots. Aberrations affect this distribution. Aberrations caused by the eye 3 often take on a no longer tolerable dimension if, in the plane of the pupil P of the eye 3, a cross-section larger than 1.5 mm in diameter is covered. Such a larger area would, however, be desirable in respect of the lateral resolution. Without spatial resolution in the conjugated pupil plane, phase differences would be mixed and averaged out in the then single detection channel when a larger pupil is utilized on the eye 3.

Figure 4:
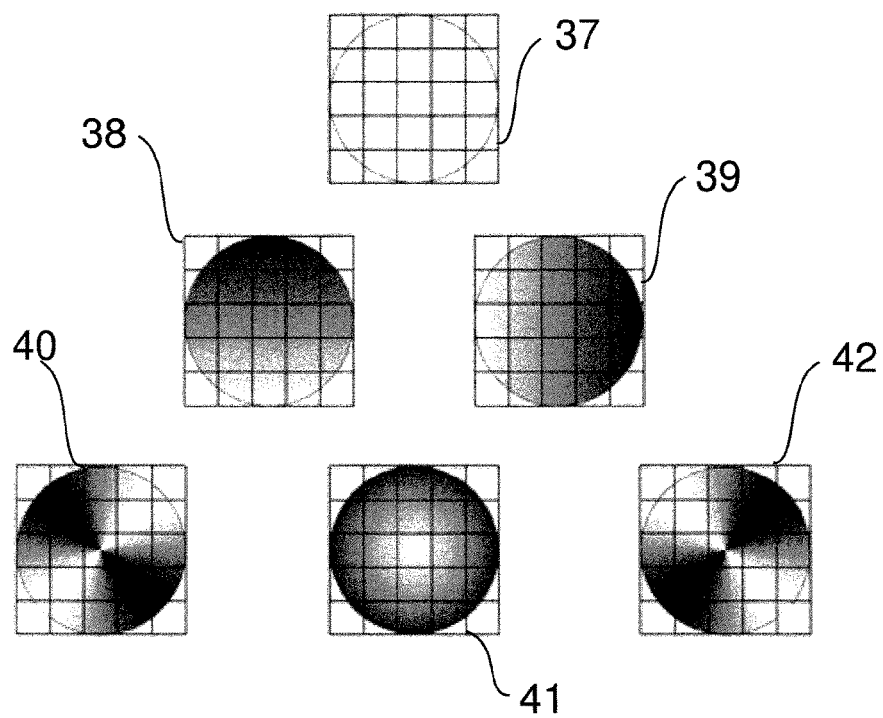

The corresponding Zernike polynomials which describe these aberrations are shown in FIG. 4, which shows top views 37 to 42 of the intensity distribution in a conjugated pupil plane. Further, a grid of the detector with 5×5 channels (or pixels) per spot is represented. The pixels sample the pupil P and thus make it possible to distinguish phase differences within the pupil P.

The maximally resolvable phase differences depend on the number of channels per spot. The inventors found out that the number of distinguishable phase differences in this plane is given by the number of channels per direction multiplied by pi. In the case of five channels per direction, as represented in FIG. 4, polynomials up to $Z_4^m$ can be distinguished per spot, wherein m can take on the values 0 (sphere), ±2 and ±4. This applies to channels that are infinitesimally small in terms of surface area. In reality, naturally, they have a particular size. Then, the measurement signal detected in a channel corresponds to an averaging of interference signal over the surface of the respective channel (e.g. pixel surface). The theoretically possible, maximum order of the Zernike polynomial can thus only be achieved if, for each spot, the phase of the signal within a channel varies less than pi. The inventors found out that, in the case of an average OCT wavelength of 1060 nm for the astigmatism caused by the eye the phase differences are recognizable with uniformly spatially distributed channels if, in the case of five channels per spot, the condition 2*pi/(5 channels per aberration period)≤pi is met. One period of minima and maxima lies within the aperture then. For higher orders, the following is true: 0.6*2*pi/(5 channels per period of the aberration)=1.2*pi/(5/1.5)≤pi for the third order and 0.5*2*pi/(5 channels per period of the aberration)=1.0*pi/(5/2)≤pi for the fourth order.

These considerations show that an area detector with at least five channels per direction and spot is capable of resolving at least the astigmatism and the third-order aberrations. A higher number of channels makes it possible to detect even higher orders of the aberration.

The above calculations took into consideration only one spatial direction. As FIG. 4 shows, the aberrations generally have a two-dimensional pattern. FIG. 4 shows, in top view 37, the first-order aberration which is also called "piston", top view 38 shows "tilt" aberration, top view 39 shows "tip" aberration, top view 41 shows "defocus" aberration and top views 40 and 42 show aberrations of "astigmatism" type. As can be seen, most aberrations have a two-dimensionally distributed pattern, whereby the phase variation is also two-dimensional. These patterns can be detected and corrected for each spot by the spatially resolving detector 19, e.g. having at least 5 channels/pixels in each direction.

The aberrations bring about, for each detector channel c, a phase $\theta_c$: $U_{sample,c} := U_{sample} * e^{i\theta_c}$. It results from a thickness δd and a refractive index δn of the material of the eye being passed through (e.g. cornea, aqueous humour, lens, vitreous humour), which in reality differs from a theoretical, aberration-free eye:

$$\theta_c(k) = \delta n(k) * k * \delta d_c$$

The detected signal is thus shifted by the aberration-related phase:

$$I_{bd,c}(k) = 4 * u_s * u_r * \cos(k * \Delta z - \delta n(k) * k * \delta d_c) = 4 * u_s u_r * \cos(k * (\Delta z - \delta n(k) \delta d_c))$$

At monochromatic radiation of 780 nm the eye causes wavefront aberrations of up to 0.7 μm, which lead to a phase shift of 2*pi (if defocus is disregarded). Such phase shift corresponds to a thickness deviation between lens and aqueous humour (these are the elements with the largest refractive index differences in the eye), which of the following value:

$$\delta d = 2pi * \frac{780 \text{ nm}}{2pi * \delta n(780 \text{ nm})} =$$

$$\frac{780 \text{ nm}}{n_{lens}(780 \text{ nm}) - n_{aqueous}(780 \text{ nm})} \approx \frac{780 \text{ nm}}{1.415 - 1.334} \approx 10 \mu m.$$

With known dispersion data, the following results:

$$\theta_c(\lambda_0 = 1060 \text{ nm}) = \frac{2pi}{1060 \text{ nm}} * (n_{lens}(1060 \text{ nm}) - n_{aqueous}(1060 \text{ nm})) * \delta d_c$$
$$= \frac{2pi}{1060 \text{ nm}} * (1.4104 - 1.3301) * 10 \mu m$$
$$= 1.516 pi$$

or $$\theta_c(k_0) = k_0 * 0.8034 \mu m.$$

If a wavelength range of Δλ=50 nm is chirped, the phase differences of the associated wave numbers ($k_0 \pm \Delta k$) are:

$$\theta_c(k_0 + \Delta k) = \frac{2pi}{1110 \text{ nm}} * (n_{lens}(1110 \text{ nm}) - n_{aqueous}(1110 \text{ nm})) * \delta d_c =$$
$$\frac{2pi}{1060 \text{ nm}} * (1.4099 - 1.3297) * 10 \mu m =$$
$$1.445 pi = (k_0 + \Delta k) * 0.8022 \mu m$$

and $$\theta_c(k_0 - \Delta k) = \frac{2pi}{1010 \text{ nm}} * (n_{lens}(1010 \text{ nm}) - n_{aqueous}(1010 \text{ nm})) * \delta d_c =$$
$$\frac{2pi}{1060 \text{ nm}} * (1.4098 - 1.3305) * 10 \mu m = 1.594 pi = (k_0 - \Delta k) * 0.8048 \mu m.$$

These calculations show that, in a sufficiently close approximation, the phase shifts which are caused by the aberrations vary linearly with the wave number k within a wavelength tuning. The detected measurement signal can thus be written as follows:

$$I_{bd,c}(k) = 4 * u_s * u_r * \cos(k * (\Delta z - \delta n(k_0) \delta d_c)).$$

Figure 8:
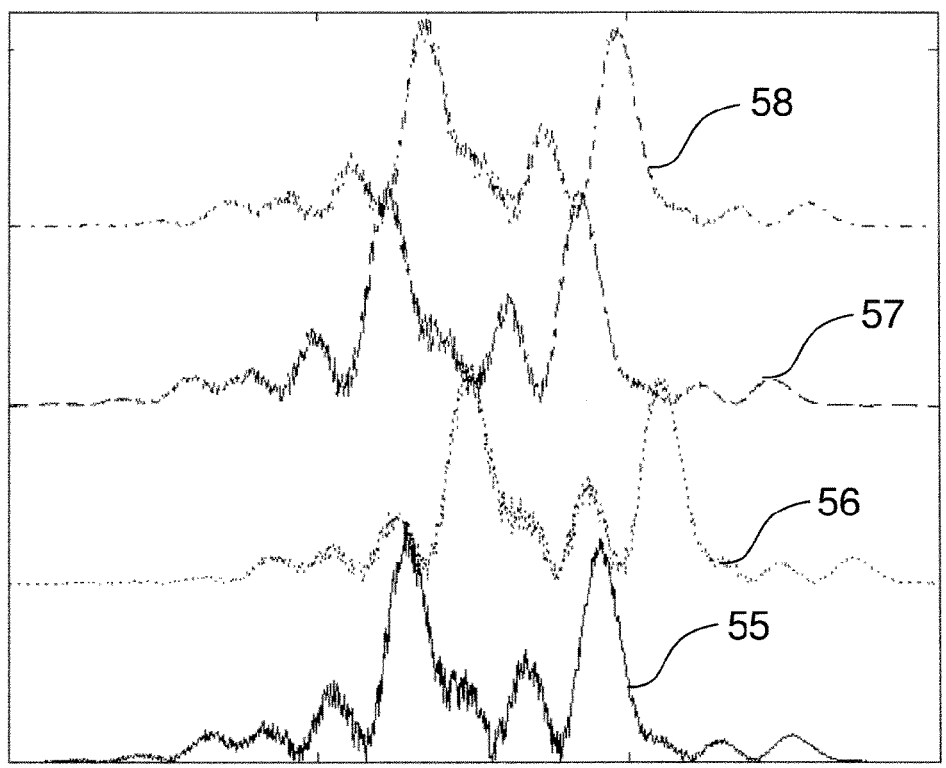

A Fourier transform for the measured wave numbers k give the axial distribution, i.e. the distribution in the z direction for the scattering tissue. Relative to an aberration-free system the axial distribution is shifted by the value $\delta n(k_0) \delta d_c$ for each channel c of the detector. FIG. 8 shows a corresponding simulation example, in which the z-coordinate is plotted on the x axis and the signal intensity is plotted on the y axis. The curves 55 to 58 correspond to four channels c of the detector. It can be assumed that, in most of tissue, variations of the axial scattering profile are small within a pupil size of 5 mm of the eye 3. Profile differences for the channels c are therefore due mainly to aberrations which shift the profile axially. It is therefore provided to relate the channel phases $\theta_c(k_0)$, caused by aberrations, to a central channel (for example the channel which lies in the centre of the detector and which corresponds to a perpendicular incidence on the sample). The measured intensities for a frequency determination are multiplied by the phase factor for correcting the aberrations. The phase factor is $e^{-i\theta_c(k_0)}$.

Each channel of the detector has a particular position relative to the retina 2. The interference signal can be recorded for each wave number $k=2*pi*n/\lambda$ during the wavelength shift/chirp of the laser, wherein n is the refractive index of the medium and $\lambda$ is the wavelength. As known to a person skilled in the art of conventional OCT systems, the measurement signals are Fourier-transformed in respect of the wave numbers, and the depth distribution of the scattering layers is calculated. The relationship $\Delta\varphi=k*\Delta z$ is used, wherein $\Delta z$ is the distance of a scattering layer from a reference layer from which the measurement radiation was transmitted to the detector along a pathlength which is identical to the pathlength of the reference radiation beam path.

Figure 6:
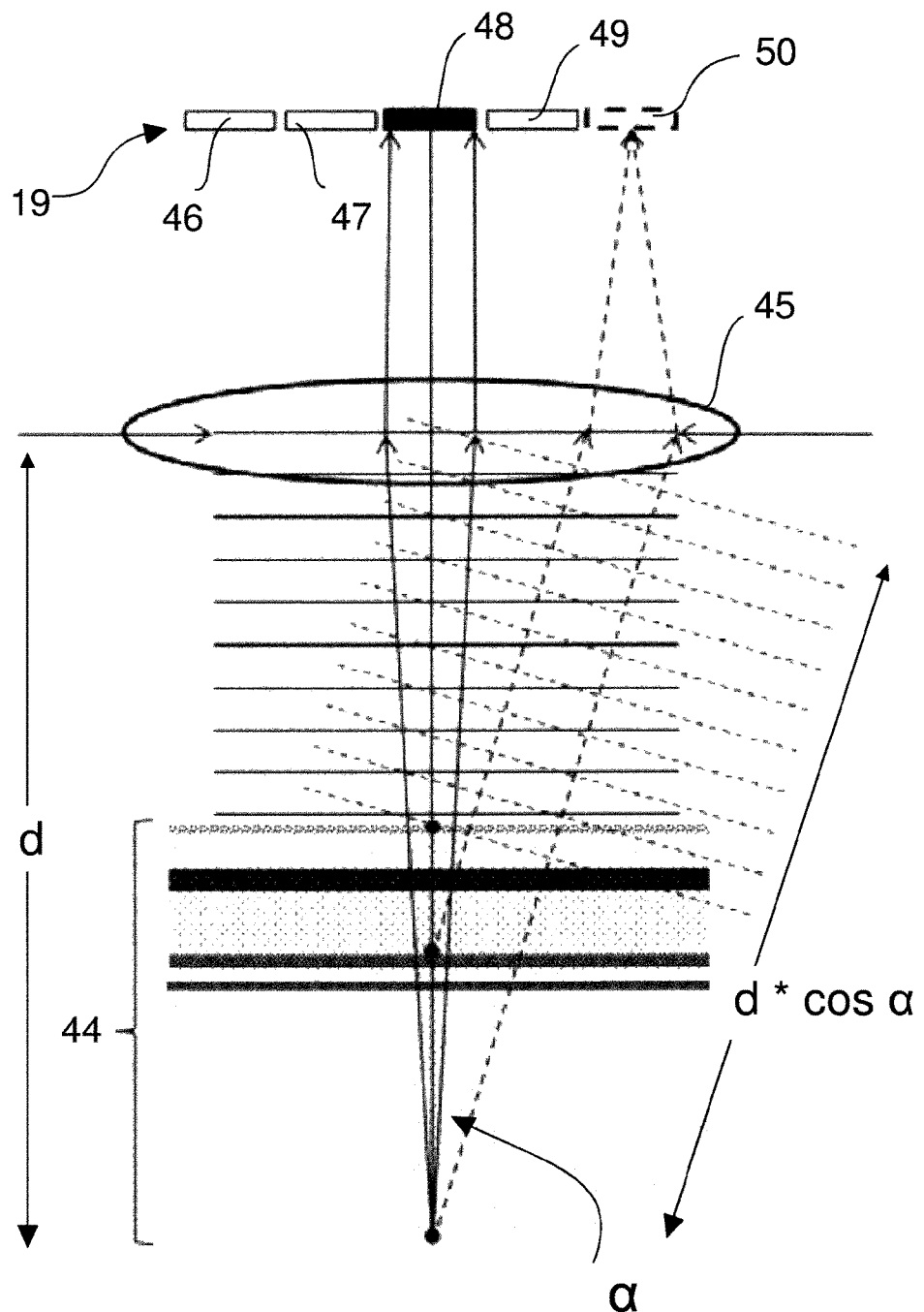
Figure 7:
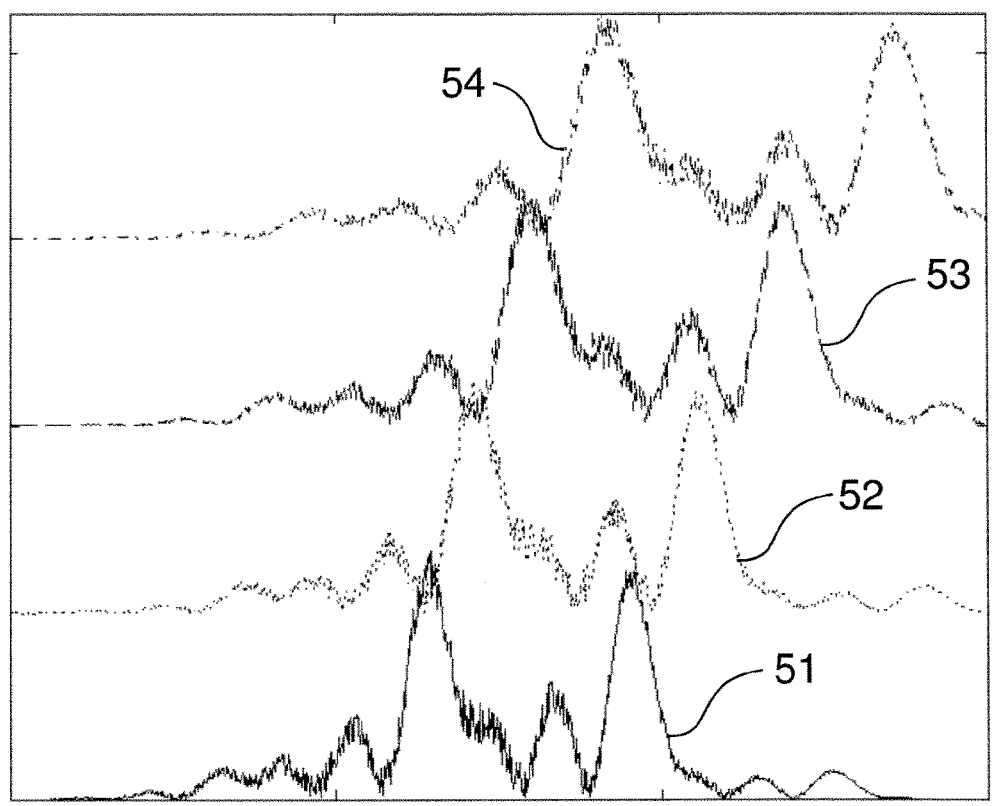

Because of the lateral extent of the detector 19 per spot, however, the optical pathlength is not identical for all pixels of a spot, as FIG. 6 shows. It can be seen there that for each spot in the detector 19, for which five pixels or channels 46, 47, 48, 49 and 50 drawn in by way of example, differ in respect of the optical pathlength from a particular point in the tissue 44 sampled by the spot. The wavefronts for central channel 48 are drawn in with continuous lines. They are perpendicular to the optical axis of the beam ray and are between the observed point, which is drawn in at the very bottom in the structure 44, and the channel 48. For this central channel 48 the beam ray runs along the optical axis. For a channel placed further out, for example outer channel 50, the main beam ray runs at an angle $\alpha$ relative to the optical axis, with the result that the path length has value d for the central channel 48 and value $d*cos(\alpha)$ for outer channel 50. For outer channel 50, FIG. 6 shows the wavefronts and main beams in dotted line. Further, FIG. 6 shows the eye lens 45 by way of example. The depth is referred to the main plane of the eye lens, as the jump in the refractive index thereof gives a reference point for the measurement. As FIG. 6 clearly shows, pixels/channels which lie further out collect radiation which covered a longer path through the medium. This has some effect on reconstruction of the image information as FIG. 7 shows by way of example. Signal curves 51 to 54 are shown there for four channels of a spot. The plotting corresponds to that of FIG. 8, i.e. the depth coordinate z is plotted on the x axis, the intensity is plotted on the y axis. As can be seen, the individual curves are not only shifted in the z direction, they are also compressed for pixels lying further out. The curve 54 is the measurement signal of the central pixel 48, and the curves 53, 52 and 51 are measurement signals from channels lying further, respectively.

A measurement error caused by this effect is corrected in an example embodiment, in order to obtain a particularly good image. The geometric effect is for example corrected by a rescaling from z to $z*cos(\alpha_c)$ for each spot, wherein $\alpha_c$ is the angle which the $c^{th}$ channel has relative to the optical axis. The angle $\alpha$ is measured against a virtual position of the detector 19 in which virtual position the detector is placed directly in front of the eye, of course, while taking into account the imaging scale. In the case of a detector which lies exactly in a plane conjugated to the pupil plane of the eye, in this way the virtual position of the detector is exactly in the plane of the pupil P of the eye 3 with dimensions of the detector modified according to the imaging scale.

During aberration correction of the reconstruction each channel is reconstructed independently. A cross-correlation is calculated in axial direction, i.e. in depth direction, in order to determine the relative phase offset between the individual channels. A reconstruction of the lateral image for each channel (optionally, as will be described below, taking into account the scanning process) and then of the phase gradient supplies a lateral offset in the image which is obtained for a given position of the scanner. This image is also called the pupil channel partial image in the following. In an embodiment the aberration is determined by application of a lateral cross-correlation of the pupil channel partial image and in this way the whole aberration phase distribution is determined and numerically corrected.

The quality of these approaches depends on the sample structure. In the case of the human eye, a very prominent axial layer structure is found. Laterally relative thereto the structures are relatively coarse, for example due to blood vessels or the papilla, combined with very fine structures, such as photoreceptors, wherein hardly any structure, with respect to size and course, lies in-between. In an example embodiment a depth correlation correction is first carried out by using the axial layer structure in order to correct the majority of the pupil phase aberrations. Optionally a lateral correlation correction follows, which utilizes lateral structures, such as for example photoreceptors, which became visible because of the first correction.

The aberrations of the eye are different at different sites on the retina. In principle it is possible to calculate the phase changes caused by aberrations in each channel for all points in a lateral image. In a simplified embodiment it is assumed that aberrations do not vary very strongly in lateral direction, and aberrations are only calculated for few lateral locations on the retina and interpolated for intermediate locations.

If a comparatively large wavelength range is tuned/chirped, it is preferred, for example, to take into account the dispersion of aberrations. In this embodiment it is not assumed that the phase shifts change linearly with the wave number k. A peak in profiles which originates in the OCT image from the retina 2 at the fundus of the eye 3 is therefore used in order to compensate for the shift of profiles relative to each other. Thus, for example, a structure (in the form of a peak) is sought in the curves 51 to 54 of FIG. 7, and the curves are corrected relative to each other using such reference structure. In this way aberrations $\theta_c(k_0)$ can be determined and corrected as described above. Alternatively a complex correlation algorithm which is applied to profiles of the different channels is also possible. In addition to a shift, a scaling (compression or expansion) of the measurement signals can also be corrected.

Each detecting status position of the scanner 13 gives a partial image of the retina, the size of which image is predefined by the diaphragm 15 (extent and hole size and number) and the front optics 12 and detector optical system 14 that cooperate during the imaging of the measurement light. A Fourier transform of the signal of the channels gives the image of the sample, but for each spot only in that part which corresponds to the size of the detected spot in the pupil. In order to generate a larger image, the scanner 13 is provided and operated, which shifts the position of the imaged object field, thus the object spots on the retina 2. The image area of each spot corresponds to a partial image 59 which has a centre 60. For a current deflection by the scanner 13 it is sufficient, for simplification, to refer to the centre 60 of the partial image 59. Scanning of multi-spot images is known to persons skilled in the art, for example in confocal microscopy. However, they are to be supplemented here to the effect that not only lateral information by adjustment of the scanner, but also depth information by tuning of the wavelength of the radiation source is obtained.

Figure 9:
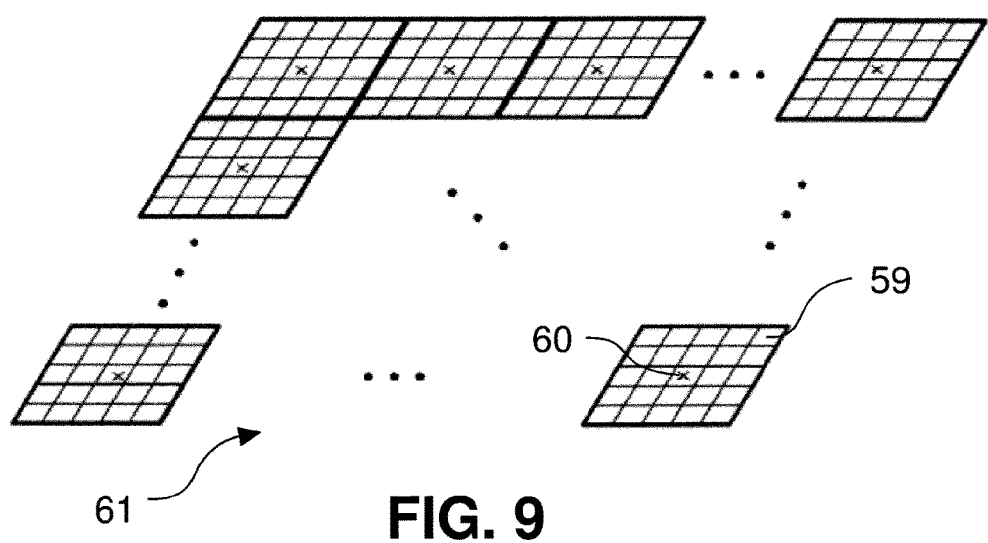
Figure 10:
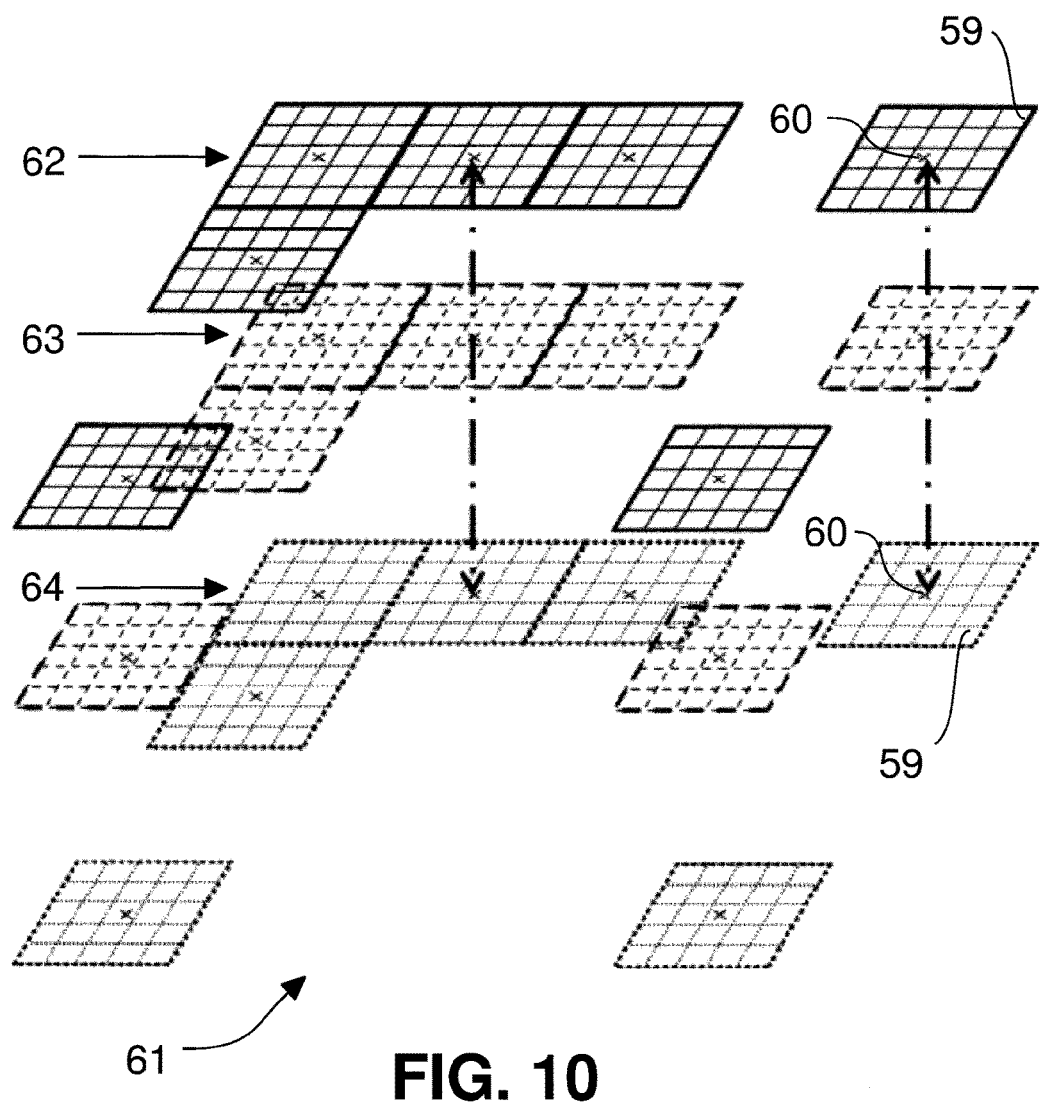
Figure 11:
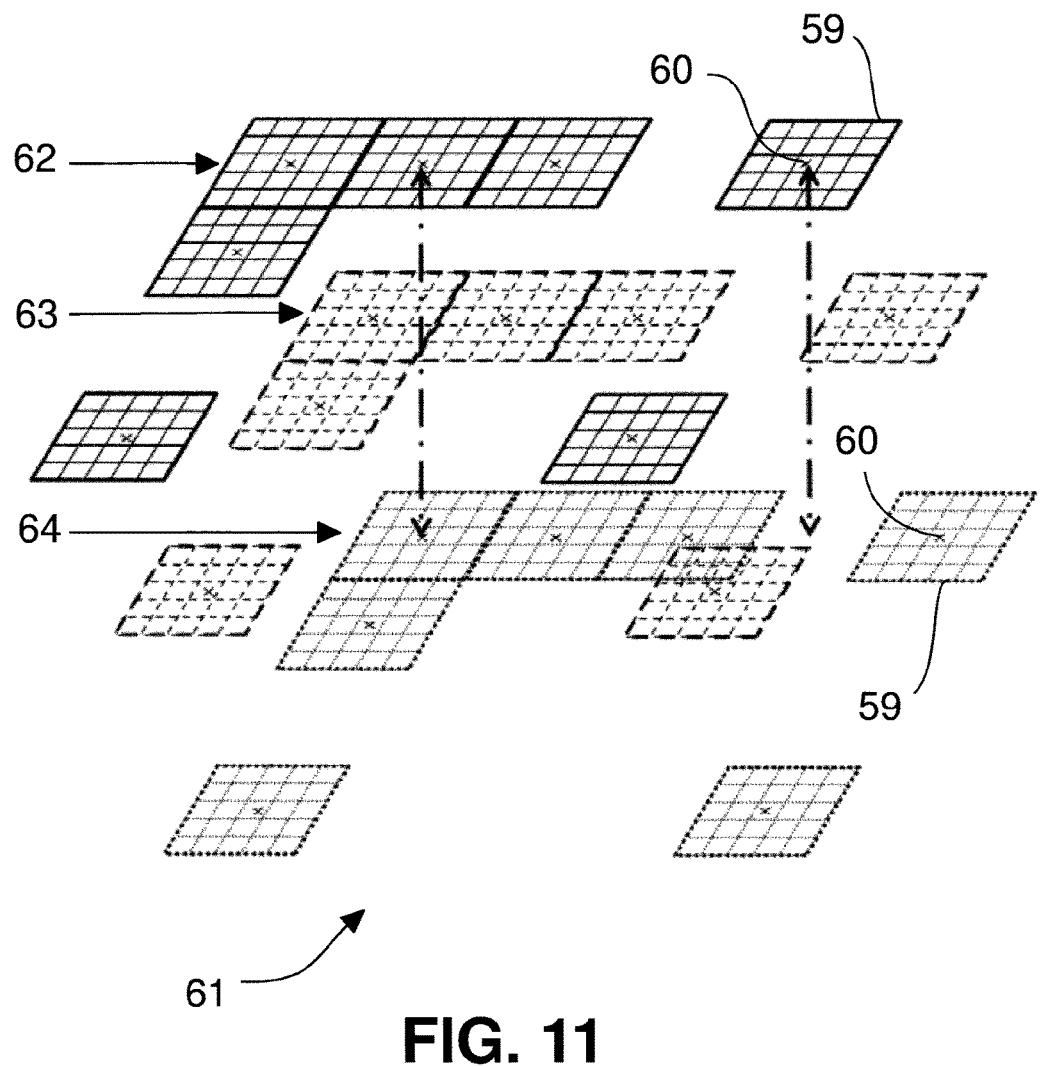

This opens different scanning approaches. The scanner can rest during the tuning of the wavelength of the light source 4. Before a renewed tuning takes place, the scanner is moved to a new position of the spot pattern, suitably spaced to the previous position. In this way the positions of the spot pattern can acquire a larger total image 61 of the retina. This approach is shown in FIG. 9 for one depth plane. As a result individual partial images 59 (each corresponding to one position of the spot pattern) are combined to the total image 61. The information of the individual depth planes then result in a three-dimensional image of a cuboid-shaped region of the retina 2. This is shown by FIG. 10, in which three planes 62, 63 and 64 are shown by way of example. The partial images 59, which are related to each other in the representation of FIG. 10 by a dot-dashed double arrow, in each case originate from a wavelength tune/chirp of the light source 4. As the scanner 13 is stationary during each wavelength tune/chirp and only adjusted in-between, the partial images 59 generated from one wavelength tune/chirp lie all with their centres 60 of the planes 62 to 64 exactly one over another.

For particular example embodiments it is preferred to scan continuously, i.e. to adjust the scanner 13 while the wavelength is tuned/chirped. This approach requires synchronization of scanner 13 and wavelength tune/chip of the light source 4. It is preferred for example, to set the lateral adjustment speed of the scanner 13 such that one wavelength tune covers at most one partial image 59 in one direction, preferably for example, not even a full image. Partial image 59 then differs from partial image of FIG. 9. In this approach the travel length of the scanner 13 can for example correspond to the spacing of the object spots, with the result that a partial image 59 corresponds exactly to the shift of the spot pattern within one period, i.e. the spacing between two neighbouring individual object spots. Thus, for planes 62, 63 and 64 the position of their centres 60 changes, as the partial images 59 in the planes are based on the different wavelengths in the Fourier transform. Unlike in the embodiment of FIG. 10 a provisional total image 61 is obtained which is not a rectangular cuboid, but e.g. a no longer rectangular parallelepiped, because of the adjustment of the scanner 13 during the wavelength tuning. An example embodiment corrects this effect for the imaging by trimming the parallelepiped down to a cuboid.

There are various possibilities for taking into account the simultaneity of wavelength tuning and lateral shift. If the detector lies close to an intermediate image plane, thus in a plane conjugated to the retina, the data of the three-dimensional parallelepiped are shifted relative to each other. For each wave number $k_i$ an image of the sample can be assembled, wherein $I_i = I(k_i, x, y)$ applies. These images $I_i$ are offset a little relative to each other. As the allocation between lateral scanning position and wave number is known, the wavelength tuning can be assembled correspondingly for each location (x, y) in the sample. In this way the three-dimensional data are simply assembled.

In embodiments in which the detector is located in or close to the conjugated pupil plane, it measures the Fourier transform of the intensity distribution in the object plane (retina 2). A shift in the object plane leads to a phase ramp in the detector plane. The correction of the simultaneous lateral adjustment by the scanner 13 and the wavelength tuning by the light source 4 is therefore obtained from a multiplication of the detector signal by a time-dependent phase ramp which is proportional to the scanning speed and the spacing between pupil partial channel and optical axis in the pupil plane.

The embodiments of FIGS. 1 to 3 have the result that the illumination and the receipt of the measurement light are no longer coupled to each other with respect to the optical properties and in particular the pupil size. In this way it is possible to fine-tune the illumination. For example, a Bessel-type illumination can be combined with a top-hat cross-sectional profile for the detection. This provides embodiments combining a large illumination depth, i.e. an illumination which is unchanged over a large z area, with high numerical aperture of the imaging. In case of an identical numerical aperture, for example with a Gaussian beam, an illumination focus with an extent of 1 mm in z direction would be achieved. In the case of a Bessel-type illumination an extent of 2 to 3 mm in the z direction is obtained. In this way the optical resolution can be increased by 10 to 30% if the detection is done with a top-hat profile.

In a further embodiment of the OCT the beam splitter 11 effects polarization splitting. This is usually considered to be disadvantageous in the state of the art, and an intensity splitting is preferred. However polarization splitting is surprisingly advantageous for the OCT of the present invention, as polarized radiation entering the eye is changed therein with respect to its polarization state. Different structures of the eye have a different polarization changing effect, with the result that the polarization state of the backscattered signal is not unambiguously or clearly defined, but consists of components with different polarization states. This consideration led the state of the art to carrying out an intensity splitting, simply because the backscattered radiation does not have a clear, defined polarization state. However, the inventors found out that only beam constituents which have the same polarization state can interfere with each other when the measurement light is superimposed with the reference light. It is the polarization state, of the reference light which predefines what portion of the measurement light can be utilized. Non-interfering portions form background noise on the detector.

The polarization splitting is now explained with reference to the embodiment of FIG. 2, but is not limited to the features otherwise realized there and can, for example, also be used in the embodiment according to FIG. 1. The illumination radiation B is linearly polarized after the polarization splitter 11. The lambda/4 plate 27, as shown in FIG. 2, generates circularly polarized illumination radiation B falling onto the eye 3. Backscattered measurement radiation M, which is likewise circularly polarized, is again linearly polarized by the lambda/4 plate, wherein the polarization direction is rotated through 90 degrees relative to the polarization direction which the illumination radiation B has which was emitted by the polarization splitter 11. The measurement radiation M thus passes through the polarization splitter 11 without deflection and interferes with the reference radiation R if the latter has the same polarization. This is the case when reference radiation R and illumination radiation B are identically linearly polarized after the dividing the source radiation. This is also the case if reference radiation R and illumination radiation B are circularly polarized after the dividing the source radiation and the reference radiation is linearly polarized identically to the measurement radiation M before the superimposition. Finally, it is important that the polarization splitting (e.g. by polarization splitter 11 and plate 27) conditions the measurement radiation M and the reference beam path conditions the reference radiation R identical to such extent that both radiations have the same polarization state on the detector.

This increases the signal-to-noise ratio, as only those parts of the measurement light that are capable of interfering with the reference light are forwarded by the beam splitter 11 to the detector device 17. Finally, the polarization splitting and rejection of a part of the measurement radiation M at the beam splitter 11, which are both disadvantageous at first glance, increase the signal quality.

In a further embodiment the OCT uses the fact that the illumination optical system 10 can to place the focus of the illumination radiation B at another z position than the focus which is predefined by the detector optical system 14 for the collection of the measurement radiation M. Because of multiple scatterings in the retina, measurement radiation M from the retina can have a pathlength suitable for interference, but can propagate in another direction, which would limit the lateral resolution in terms of the depth. This effect can be compensated for by different focal depth planes for illumination and detection. The depth resolution is optimized.

For image reconstruction from the detector signals the current wavelength must be known according to the FD-OCT principle. This wavelength or the corresponding wavenumber k can be derived from control of the light source 4. Alternatively it is possible to couple out a beam portion and detect its wavelength, in order to better know the current wavelength or the status of the wavelength chirp.

Perpendicularly to the sampling direction, detector channels can be combined in order to reduce speckles. This is particularly advantageous if only z-sections through the retina are desired.

For a coarsely resolved image, e.g. for a preview image, it is possible to combine all or several detector channels for each spot. This can be done after the corrections (e.g. aberration, z-position, total image generation). Resolution of conventional OCT systems is then obtained, however, with a higher signal-to-noise ratio and improved speckle behaviour, simply because the combination is done after one or more of the corrections and thus goes beyond a normal pixel binning.

If a detector is used which is only spatially resolving in one direction, aberrations can be corrected in this direction only. This may be sufficient for particular applications.

In an embodiment an iris camera is provided which assists the operator to adjust the device at the eye.

For all embodiments of the described optical coherence tomographs or methods for optical coherence tomography, the following example developments can be advantageously used:

Phase errors which form if detector 19, 19a, 19b is not located exactly in the focal plane of the microlenses of the multi-lens array 36, 36a, 36b can be corrected numerically.

The microlenses of the multi-lens array and thus ultimately the illumination spots on the retina 2 can be arranged in a square grid or in a hexagonal grid. As, for the multi-hole diaphragms, round openings are preferred, for example, and the pupil or detection aperture as a rule is approximately round, a hexagonal grid enables a further saving of detection pixels, i.e. allows to utilize detectors with fewer pixels.

It is preferred, in an example embodiment, to have, independently of the grid of the illumination spots on the retina 2, one pixel of the area detector 19, 19a, 19b precisely in the centre of each imaged spot. In the case of a hexagonal grid of the illumination spots in combination with a rectangular grid of the pixels of detector 19, 19a, 19b, therefore, the size of the holes of the multi-hole diaphragm 34 and thus also of the multi-hole diaphragms 15, 15a, 15b should be matched to the pixel size and the resolution of detector 19, 19a, 19b such that this condition is met sufficiently, i.e. at least approximately, e.g. to +/−10% of the spot diameter.

Where method steps and/or signal corrections were described above, these are carried out in the OCT 1 by the control device C which is connected to the detector, reads its measurement signals and obtains further data about the operation of the scanner 13 and the wavelength tuning and/or controls these components correspondingly.

The invention claimed is:

1. An optical coherence tomograph for examining a scattering sample to be placed in an object area, the optical coherence tomograph comprising:
   an illumination source that emits source radiation of sweepable wavelength;
   a dividing element that divides the source radiation into a reference beam path and an illumination beam path for illuminating the object area with illuminating radiation;
   optics in the illumination beam path that distribute the illumination radiation into several object spots and that project these object spots to the object area, and a scanner that adjusts the lateral position of the object spots in the object area;
   a detection beam path collecting radiation scattered at the object spots as measurement radiation and superimposing this measurement radiation with reference radiation guided through the reference beam path and guiding the superimposed radiations to a spatially resolving detector comprising pixels, wherein the measurement radiation from an individual object spot is guided to a detector spot covering several pixels of the detector with the detector generating signals therefrom; and
   a control device processing the signals generated by the detector and generating therefrom an image of a sample provided in the object area.

2. The optical coherence tomograph according to claim 1, wherein the optics comprise a multi-lens array that distributes the illumination a into the several object spots.

3. The optical coherence tomograph according to claim 1, wherein the optics comprise a first multi-hole diaphragm that distributes the illumination radiation into the several object spots.

4. The optical coherence tomograph according to claim 1, wherein the detection beam path comprises a second multi-hole diaphragm defining an object spot field size for the individual objects spots in the object area, from which object spot fields measurement radiation reaches the detector.

5. The optical coherence tomograph according to claim 4, wherein the second multi-hole diaphragm is located in or close to an intermediate image plane of the collecting of measurement radiation.

6. The optical coherence tomograph according to claim 1, wherein a multi-lens array is located upstream of the detector, which multi-lens array bundles radiation from each object spot to the assigned detector spot.

7. The optical coherence tomograph according to claim 1, wherein the detector is located in an image plane of the collecting of the measurement radiation.

8. The optical coherence tomograph according to claim 1, wherein the detector is located in a far field of the object area.

9. The optical coherence tomograph according to claim 1, wherein the detection beam path comprises a beam splitter that splits the illumination radiation from the measurement radiation scattered in the object area.

10. The optical coherence tomograph according to claim 9, wherein the beam splitter comprises a polarizing beam splitter and a lambda/4 plate is located between the object area and the beam splitter, the lambda/4 plate cooperating with the polarizing beam splitter to filter the measurement radiation regarding a polarization state of the measurement radiation.

11. The optical coherence tomograph according to claim 1, wherein the illumination beam path comprises an optical element which acts on the illumination radiation only and which defines the numerical aperture of illuminating the object area independently from the numerical aperture of collecting the measurement radiation.

12. The optical coherence tomograph according to claim 1, wherein the reference beam path comprises a multi-lens array which bundles the reference radiation into a multi-spot pattern adapted to the object spots at which the measurement radiation is collected.

13. The optical coherence tomograph according to claim 1, wherein the scanner shifts the lateral position of the spots during a wavelength sweep of the source radiation and generates a scan signal indicating a deflection status of the scanner, wherein the control device is connected to the scanner and to the radiation source and reads out a wavelength signal indicating an actual wavelength of the source radiation and consequently of the illumination radiation and connected to the detector and reads out measurement signals for each pixel, wherein the control device generates from the wavelength signal and the measurement signals partial images of a sample located in the object area and evaluates the scan signal to combine the partial images into a 3D total image.

14. The optical coherence tomograph according to claim 1, wherein the sample examined comprises a human eye.

15. The optical coherence tomograph according to claim 14, wherein the sample examined comprises a retina of the human eye.

16. The optical coherence tomograph according to claim 14, wherein the illumination radiation is uniformly distributed over a cross section covered in the pupil of the eye, however, allowing for intensity fluctuations of +/−10%.

17. The optical coherence tomograph according to claim 1, wherein,
the optical coherence tomograph is structured to examine the retina;
the illumination beam path comprises a light-distributing element that distributes the illumination radiation over the spots and that illuminates the retina,
the illumination and measurement beam path comprise a shared front optic and a shared beam splitter that split off the measurement radiation collected at the eye from the illumination radiation guided to the eye, wherein the beam splitter guides the split off measurement radiation to the detection beam path,
the reference beam path provides an optical path length for the reference radiation, which optical path length corresponds to an optical distance from the splitting element to the object spots and back to a point of superposition, and
the detection beam path superimposes the measurement radiation and the reference radiation at the point of superposition and comprises an optical element acting only on the measurement radiation and co-operating with the front optics to define the numerical aperture with which measurement radiation is collected from the eye, wherein further a diaphragm is located upstream of the detector and in or close to an intermediate image plane and defines the size of an object field from which measurement radiation reaches the detector,
wherein the diaphragm upstream of the detector is formed as a first multi-hole diaphragm and a first multi-lens array is located between the first multi-lens diaphragm and the detector, the first multi-lens array bundles radiation emerging from each hole of the first multi-diaphragm onto a dedicated pixel area of the detector which presents a spatial resolution of 4 to 100 pixels in one direction.

18. The optical coherence tomograph according to claim 17, wherein the dedicated pixel area presents a spatial resolution of 2D pixel area of 5 to 50 pixels or of 5 to 40 pixels per direction.

19. A method for optical coherence tomography for examining a sample, including an eye, wherein the method comprises:
providing source radiation, sweeping the wavelength thereof and dividing the source radiation into illumination radiation and reference radiation;
illuminating the sample with the illumination radiation at a multitude of object spots, wherein a scanner is used for shifting the lateral position of the object spots;
guiding the reference radiation through a reference beam path;
collecting illumination radiation backscattered in or at the sample in a form of measurement radiation by imaging the object spots to detector spots;
superimposing the measurement radiation with reference radiation guided through the reference beam path, wherein the detector spots are fed with superimposed radiation; and
the detecting an intensity distribution of the detector spots.

20. The method according to claim 19, further comprising performing imaging of the detector spots in parallel by filtering the measurement radiation with a multi-hole diaphragm.

21. The method according to claim 19, further comprising detecting of the intensity distribution by oversampling in which a resolution of the intensity distribution of each detector spot assigned to an object spot is larger than a resolution of illuminating of the sample with the illumination radiation at the multitude of object spots.

22. The method according to claim 21, further comprising obtaining an image correction from the intensity distribution.

23. The method according to claim 19, further comprising generating the multitude of object spots by using a multi-lens array.

24. The method according to claim 19, further comprising generating the multitude of object spots by using a first multi-hole diaphragm.

25. The method according to claim 19, further comprising imaging the objects spots to the detector spots by using a second multi-lens diaphragm defining a size of object spot fields of the individual detector spots in the sample, and detecting the measurement radiation from the object spot fields.

26. The method according to claim 19, further comprising locating the second multi-hole diaphragm close or in an intermediate image plane of the imaging.

27. The method according to claim 19, further comprising providing a multi-lens array upstream of a detector comprising pixels, wherein the multi-lens array bundles each detector spot to several pixels of the detector.

28. The method according to claim 19, further comprising detecting the intensity distribution of the detector spots in an image plane of the imaging of the object spots.

29. The method according to claim 19, further comprising detecting the intensity distribution of the detector spots in a far field of the sample.

30. The method according to claim 19, further comprising separating the illumination radiation from the measurement radiation scattered in the sample by using a beam splitter.

31. The method according to claim 30, further comprising making or selecting the beam splitter to be a polarizing beam splitter and further comprising locating a lambda/4 plate between the object field and the beam splitter and wherein the lambda/4 plate cooperates with the polarizing beam splitter to filter the measurement radiation regarding a polarization of the measurement radiation.

32. The method according to claim 19, further comprising independently setting the numerical aperture of the imaging of the object field separate from the numerical aperture of the collecting of the measurement radiation.

33. The method according to claim 19, further comprising bundling the reference radiation to a multi-spot pattern which is adapted to the object spots at which the measurement radiation is collected.

34. The method according to claim 19, further comprising shifting the lateral position of the spots during wavelength sweeps of the source radiation and generating partial images of the object based on the wavelength of the source radiation and consequently of the illuminating radiation and based on the detected intensity distribution, and composing the partial images to a 3D total image under consideration of the shift of the lateral position of the spots.

35. The method according to claim 19, further comprising selecting the sample examined to be a human eye.

36. The method according to claim 35, further comprising selecting the sample examined to be a retina.

37. The method according claim 35, further comprising uniformly distributing the illumination radiation over the pupil of the eye within a cross section covered by the illumination radiation, however, allowing for intensity fluctuations of not more than +/−10%.

* * * * *

UNITED STATES PATENT AND TRADEMARK OFFICE
CERTIFICATE OF CORRECTION

PATENT NO. : 10,244,940 B2
APPLICATION NO. : 15/546365
DATED : April 2, 2019
INVENTOR(S) : Daniel Bublitz et al.

Page 1 of 1

It is certified that error appears in the above-identified patent and that said Letters Patent is hereby corrected as shown below:

In the Specification

Column 9, Lines 21-22, please delete the existing formula and insert the following:
-- $I_2 = |U_{sample} + U_{reference} * e^{in}|^2$
$= |U_{sample}|^2 + |U_{reference}|^2 + 2Re\{U_{sample} * \bar{U}_{reference} * e^{-in}\}$ --

Column 16, Lines 3-4, please delete the existing formula and insert the following:
-- $I_{bd,c}(k) = 4 * u_s * u_r * \cos(k * \Delta z - \delta n(k) * k * \delta d_c)$
$= 4 * u_s * u_r * \cos(k * (\Delta z - \delta n(k) \delta d_c))$ --

Signed and Sealed this
Tenth Day of December, 2019

Andrei Iancu
*Director of the United States Patent and Trademark Office*

UNITED STATES PATENT AND TRADEMARK OFFICE
CERTIFICATE OF CORRECTION

PATENT NO. : 10,244,940 B2
APPLICATION NO. : 15/546365
DATED : April 2, 2019
INVENTOR(S) : Daniel Bublitz et al.

Page 1 of 1

It is certified that error appears in the above-identified patent and that said Letters Patent is hereby corrected as shown below:

In the Specification

Column 9, Lines 21-22, please delete the existing equation and insert the following equation:

$$I_2 = \left|U_{sample} + U_{reference} * e^{i\pi}\right|^2 = \left|U_{sample}\right|^2 + \left|U_{reference}\right|^2 + 2Re\{U_{sample} * \overline{U}_{reference} * e^{-i\pi}\}$$
--

Signed and Sealed this
Ninth Day of June, 2020

Andrei Iancu
*Director of the United States Patent and Trademark Office*